US007507233B2

(12) United States Patent
Littrup et al.

(10) Patent No.: US 7,507,233 B2
(45) Date of Patent: Mar. 24, 2009

(54) CRYOTHERAPY SYSTEM

(75) Inventors: Peter J. Littrup, Bloomfield Hills, MI (US); Alexei V. Babkin, Albuquerque, NM (US); Robert Duncan, Tijeras, NM (US); Sergey Boldarev, Moscow (RU)

(73) Assignee: Cryo Dynamics, LLC, Bloomfield Hills, MI (US)

( * ) Notice: Subject to any disclaimer, the term of this patent is extended or adjusted under 35 U.S.C. 154(b) by 267 days.

(21) Appl. No.: 11/447,356

(22) Filed: Jun. 6, 2006

(65) Prior Publication Data

US 2006/0235375 A1     Oct. 19, 2006

Related U.S. Application Data

(62) Division of application No. 10/757,769, filed on Jan. 14, 2004, now Pat. No. 7,083,612.

(60) Provisional application No. 60/440,662, filed on Jan. 15, 2003.

(51) Int. Cl.
     *A61B 18/18*      (2006.01)
(52) U.S. Cl. ...................................................... 606/20
(58) Field of Classification Search .............. 606/20–26
     See application file for complete search history.

(56) References Cited

U.S. PATENT DOCUMENTS

| 3,613,689 A | 10/1971 | Crump |
|---|---|---|
| 3,942,010 A | 3/1976 | Peterson |
| 3,993,123 A | 11/1976 | Chu |
| 4,034,251 A | 7/1977 | Haas |
| 4,167,771 A | 9/1979 | Simons |
| 4,226,281 A | 10/1980 | Chu |
| 4,281,268 A | 7/1981 | Sawa |
| 4,384,360 A | 5/1983 | Kitadate |
| 4,418,421 A | 11/1983 | Kitadate |
| 4,519,389 A | 5/1985 | Gudkin |
| 4,802,475 A | 2/1989 | Weshahy |
| 4,838,041 A | 6/1989 | Bellows |
| 4,843,446 A | 6/1989 | Nishino |
| 4,945,562 A | 7/1990 | Staub |

(Continued)

FOREIGN PATENT DOCUMENTS

WO     WO 02/096270     12/2002

(Continued)

*Primary Examiner*—Roy D. Gibson
*Assistant Examiner*—Peter J Vrettakos
(74) *Attorney, Agent, or Firm*—Lawrence N. Ginsberg; Townsend and Townsend and Crew LLP

(57) ABSTRACT

A cryotherapy system is provided with multiple cryoprobes, each of which has a shaft with a closed distal end adapted for insertion into a body and conduits for flowing a cryogenic fluid through the shaft to reduce a temperature of the distal end. A source is provided for the cryogenic fluid, and flow-control metering valves are provided in fluid communication with the conduits and source of the cryogenic fluid. A compressor is provided in fluid communication with the conduits of the cryoprobes to define a self-contained fluid system. The flow-control metering valves and the compressor are controlled by a computer processor to provide the desired flows of the cryogenic fluid through the conduits of the self-contained fluid system.

8 Claims, 9 Drawing Sheets

U.S. PATENT DOCUMENTS

| | | | |
|---|---|---|---|
| 4,946,460 | A | 8/1990 | Merry |
| 4,982,080 | A | 1/1991 | Wilson |
| 5,012,505 | A | 4/1991 | Zupancic |
| 5,155,093 | A | 10/1992 | Den |
| 5,173,606 | A | 12/1992 | Weinberger |
| 5,212,626 | A | 5/1993 | Bell |
| 5,254,116 | A | 10/1993 | Baust |
| 5,274,237 | A | 12/1993 | Gallagher |
| 5,334,181 | A | 8/1994 | Rubinsky |
| 5,405,533 | A | 4/1995 | Hazleback |
| 5,417,072 | A | 5/1995 | Silver |
| 5,433,717 | A | 7/1995 | Rubinsky |
| 5,471,844 | A | 12/1995 | Levi |
| 5,494,039 | A | 2/1996 | Onik |
| 5,504,924 | A | 4/1996 | Ohashi |
| 5,531,742 | A | 7/1996 | Barken |
| 5,741,248 | A | 4/1998 | Stern |
| 5,757,885 | A | 5/1998 | Yao |
| 5,800,487 | A | 9/1998 | Mikus |
| 5,800,488 | A | 9/1998 | Crockett |
| 5,816,052 | A | 10/1998 | Foote |
| 5,899,897 | A | 5/1999 | Rabin |
| 5,901,783 | A | 5/1999 | Dobak, III |
| 5,910,104 | A | 6/1999 | Dobak, III |
| 5,916,212 | A | 6/1999 | Baust |
| 5,924,975 | A | 7/1999 | Goldowsky |
| 5,947,960 | A | 9/1999 | Griswold |
| 5,950,444 | A | 9/1999 | Matsunaga |
| 5,957,963 | A | 9/1999 | Dobak |
| 5,978,697 | A | 11/1999 | Maytal |
| 5,993,444 | A | 11/1999 | Ammar |
| 6,039,730 | A | 3/2000 | Rabin |
| 6,074,412 | A | 6/2000 | Mikus |
| 6,139,544 | A | 10/2000 | Mikus |
| 6,142,991 | A | 11/2000 | Schatzberger |
| 6,179,831 | B1 | 1/2001 | Bliweis |
| 6,190,378 | B1 | 2/2001 | Jarvinen |
| 6,193,644 | B1 | 2/2001 | Dobak, III |
| 6,235,018 | B1 | 5/2001 | LePivert |
| 6,251,105 | B1 | 6/2001 | Mikus |
| 6,263,046 | B1 | 7/2001 | Rogers |
| 6,307,916 | B1 | 10/2001 | Rogers |
| 6,377,659 | B1 | 4/2002 | Snyder |
| 6,396,901 | B1 | 5/2002 | Heil |
| 6,451,011 | B2 | 9/2002 | Tu |
| 6,471,694 | B1 | 10/2002 | Kudaravalli |
| 6,475,212 | B2 | 11/2002 | Dobak, III |
| 6,477,231 | B2 | 11/2002 | Snyder |
| 6,530,420 | B1 | 3/2003 | Takada |
| 6,544,176 | B2 | 4/2003 | Mikus |
| 6,584,332 | B2 | 6/2003 | Yoshitake |
| 6,602,276 | B2 | 8/2003 | Dobak, III |
| 6,622,494 | B1 | 9/2003 | Pourrahimi |
| 6,622,507 | B2 | 9/2003 | Cotte |
| 6,628,002 | B2 | 9/2003 | Ritz |
| 6,648,879 | B2 | 11/2003 | Joye et al. |
| 6,706,037 | B2 | 3/2004 | Zvuloni |
| 6,812,464 | B1 | 11/2004 | Sobolewski |
| 2001/0024485 | A1 | 9/2001 | Rogers |
| 2002/0040220 | A1 | 4/2002 | Zvuloni |
| 2002/0062831 | A1 | 5/2002 | Beyar |
| 2002/0087152 | A1 | 7/2002 | Mikus |
| 2002/0151331 | A1 | 10/2002 | Abdelmonem |
| 2004/0027462 | A1 | 2/2004 | Hing |
| 2004/0118144 | A1 | 6/2004 | Hsu |
| 2004/0163797 | A1 | 8/2004 | Cosley |
| 2004/0218725 | A1 | 11/2004 | Radley |

FOREIGN PATENT DOCUMENTS

| | | |
|---|---|---|
| WO | WO 2004/064914 | 8/2004 |

CRYOTHERAPY SYSTEM

CROSS-REFERENCES TO RELATED APPLICATIONS

This application is a divisional application of, and claims the benefit of the filing date of U.S. patent application Ser. No. 10/757,769, now U.S. Pat. No. 7,083,612 entitled "CRYOSURGICAL SYSTEM," filed Jan. 14, 2004, which was a nonprovisional application of, and claimed the benefit of U.S. Prov. Pat. Appl. No. 60/440,662, entitled "CRYOSURGICAL SYSTEM," filed Jan. 15, 2003 by Peter Littrup et al., the entire disclosure of which is incorporated herein by reference for all purposes, including the appendices.

This application is related to concurrently filed, commonly assigned U.S. patent application Ser. No. 10/757,768, entitled "CRYOTHERAPY PROBE," by Peter Littrup et al., which is a nonprovisional application of U.S. Prov. Pat. Appl. No. 60/440,541, entitled "CRYOSURGICAL PROBE," filed Jan. 15, 2003 by Peter Littrup et al., the entire disclosures of both of which are incorporated herein by reference for all purposes, including the appendices.

BACKGROUND OF THE INVENTION

This invention relates to generally to cryotherapy. More specifically, this application relates to image-guided control of cryoprobes and cryocoolers by a separate self-contained cryotherapy system.

Cryotherapy probes are used to treat a variety of diseases. The cryotherapy probes quickly freeze diseased body tissue, causing the tissue to die, after which it will be absorbed by the body or expelled by the body or sloughed off. Cryotherapy has traditionally been used within the operative setting to freeze liver and prostate tumors. Intraoperative ultrasound provided sufficient guidance for probe placement and progression of the ice front in relation to tumor margins. Cryotherapy for multiple outpatient treatments has a long history, due in part to its relatively painless delivery and ability to treat pain syndromes. The transition to outpatient cancer treatments requires rapidly freezing probes along with a convenient cryotherapy system. Without a relatively small, self-contained, easy-to-use cryosystem employing lower priced probes (i.e., currently each Endocare probe costs ~$400-1500), the patient benefits of cryotherapy (i.e., lower pain, clear imaging of ablation zone and minimal scarring) will not adequately challenge the current popularity enjoyed by heat-based systems. For example, radiofrequency (RF) ablation has become the most common ablation modality perhaps more for its convenient set-up for physicians and lower disposable costs for hospital administrators than any distinct benefit over cryotherapy.

Percutaneous cryotherapy (PC) for breast, liver, kidney, bone and lung tumors has recently been described by Littrup, et al., copies of which are attached as Appendices A and B of U.S. Prov. Pat. Appl. Nos. 60/440,541 and 60/440,662, both of which have been incorporated by reference. PC monitoring is more difficult with standard ultrasound since it visualizes the treatment site from limited external positions. Therefore, CT and MRI have become the PC guidance modalities of choice due to their circumferential imaging and multi-slice rendering of a three dimensional volume. The phase change that occurs when tissue freezes (and resultant necrotic treatment margins) is much better seen by US, CT or MRI than the ablation margins of heat-based therapies. In addition, the necrotic treatment margin is much smoother and more predictable for ice than heat. When compared to heat-based ablation techniques, PC treatments are relatively painless and better preserve the underlying collagenous architecture of the ablated tissue. This produces better healing and less tissue disruption during, or after, the procedure. As long as bowel and major nerves are avoided, PC cancer treatments can be performed with safety of adjacent tissues via accurate treatment planning.

Adequate coverage of the tumor by ice, but with minimal side-effects, often requires several accurately placed cryoprobes. Multiple patents and applications have been published which attempt to address these issues. These cover cryoprobe design or freeze method [Cryomedical Sciences (U.S. Pat. Nos. 5,254,116 and 5,334,181); Endocare (U.S. Pat. Nos. 5,800,487 and 5,800,488); Cryogen (U.S. Pat. Nos. 5,910,104 and 6,475,212); Galil (U.S. Pat. Nos. 6,142,991 and 6,179,831)], computer controlled/interaction [Endocare (U.S. Pat. No. 6,139,544 and U.S. Pat. Publ. No. 2002/0016540A1); Cryogen (U.S. Pat. Nos. 5,513,742 and 6,471,694)] or MRI guidance [Galil (U.S. Pat. No. 5,978,697)]. Each of the foregoing patents and publications is incorporated herein by reference for all purposes. The Cryomedical Sciences efforts attempted to combat the flow difficulties encountered by liquid nitrogen ($LN_2$) in smaller probes (e.g., $\leq 3$ mm) but required a highly complex system using large $LN_2$ volumes. While the Cryogen patents referred to a closed-loop gas system, no thermodynamic optimization was described to reduce engineering complexity. Therefore, companies with units which use large flow rates, or amounts of gas, to produce maximal freeze capacity per probe generally acknowledge the desire for an open system since the required compressors for such closed systems would become too large, expensive and unwieldy for portable use. In addition, the lack of optimized cryogenic design and probe configuration to produce the greatest freeze power for the minimal gas flow configuration prevents the design of smaller (i.e., <1.5 mm) probe diameters. While Galil has a 1.5 mm probe, its freeze capacity remains less than the Endocare 2.4 mm probe.

A combined effort is needed to optimize cryoprobes and the main driving system. A variety of cryotherapy instruments, variously referred to as cryoprobes, cryotherapy ablation devices, cryostats and cryocoolers, have become available. Currently preferred cryotherapy systems use Joule-Thomson (JT) cooling in devices known as JT cryostats. These devices take advantage of the fact that non-ideal gases, when rapidly expanded, become extremely cold. In these devices, a high pressure gas such as argon or nitrogen is expanded through a nozzle inside a small cylindrical sheath made of steel, and the JT expansion cools the steel sheath to sub-freezing cryogenic temperature very rapidly. An exemplary device is illustrated in U.S. Pat. No. 3,800,552, the entire disclosure of which is herein incorporated by reference for all purposes. This patent shows a basic Joule-Thomson probe with a sheath made of metal, a fin-tube helical gas supply line leading into a Joule-Thomson nozzle which directs expanding gas into the probe. Expanded gas is exhausted over the fin-tube helical gas supply line, and pre-cools incoming high pressure gas in what is known as a 'counterflow heat exchanger'. The counterflow heat exchanger is beneficial because by pre-cooling incoming gas with the outgoing gas flow the probe obtains lower temperatures.

U.S. Pat. No. 5,522,870, the entire disclosure of which is herein incorporated by reference for all purposes, applies the general concepts of Joule-Thomson devices to a device which is used first to freeze tissue and then to thaw the tissue with a heating cycle. Nitrogen is supplied to a Joule-Thomson nozzle for the cooling cycle, and helium is supplied to the same Joule-Thomson nozzle for the warming cycle. Preheating of the helium is used to provide warming to a sufficiently high temperature. Furthermore, since the helium gas inversion temperature of approximately −240° C. is well below the base temperature of liquid nitrogen (−193° C.) helium is essentially an ideal gas at −240° C. and higher temperatures, and hence it does not cool during the gas expansion process. Various cryocoolers use mass flow warming, flushed backwards through the probe, to warm the probe after a cooling cycle [Lamb, Refrigerated Surgical Probe, U.S. Pat. No. 3,913,581; Longsworth, Cryoprobe, U.S. Pat. No. 5,452,582]. Each of these patents is also incorporated herein by reference for all purposes. A deficiency to broad adoption of gas-based systems by physicians and hospitals appears to be their lack of efficient self-contained systems.

Finally, cryotherapy needs to be considered as an adjuvant, or complementary, treatment with other cancer therapies. Successful reports from many papers on image-guided tumor ablation (including both heat-based and cryotherapy) were noted at the Radiological Society of North America's annual meeting for 2002 and 2003. Several prominent radiologists considered it to be "the fourth branch of oncology", in conjunction with surgery, radiation therapy and chemotherapy. Littrup, et al, have also noted the possible potentiation of cryotherapy, as well as reduced bleeding risk, by pre-injecting the region to be frozen with macro-aggregated albumin (MAA), hypertonic saline and epinephrine. This technique has been described by Dr. Order for treatment of pancreatic cancer with $P^{32}$, whereby the MAA creates an interstitial 'gel' effect and thus decreases subsequent fluid extravasation of the $P^{32}$ out of the tumor injection site (U.S. Pat. Nos. 5,538,726 and 5,424,288). In addition, injection of radiotherapeutic, or chemotherapeutic, agents directly into the tumor before or after the freeze may provide more thorough tumor ablation. Combining cryotherapy with radiation therapy, or chemotherapy, may reduce the overall risks of either chemotherapy or radiation therapy alone. Therefore, probe modifications which could deliver fluid through the probe, associated sheath system, or separate probe injection system would be of distinct benefit for future cryotherapy applications. In addition, probe modifications to allow minimal size with injection capacity would also benefit and re-invigorate the interest in PC for localized nerve ablation in pain management.

BRIEF SUMMARY OF THE INVENTION

Embodiments of the invention thus provide a cryotherapy system that avoids certain deficiencies of the prior art. The cryotherapy system includes a plurality of cryoprobes, each of which has a shaft with a closed distal end adapted for insertion into a body and conduits for flowing a cryogenic fluid through the shaft to reduce a temperature of the distal end. A source is provided for the cryogenic fluid, and a plurality of flow-control metering valves is provided in fluid communication with the conduits of the plurality of cryoprobes and with the source of the cryogenic fluid. A compressor is provided in fluid communication with the conduits of the plurality of cryoprobes to define a self-contained fluid system. The plurality of flow-control metering valves and the compressor are controlled by a computer processor to provide the desired flows of the cryogenic fluid through the conduits of the self-contained fluid system.

In some embodiments, the self-contained fluid system is an open-loop system, while in other embodiments it is a closed-loop system. Furthermore, in different embodiments, the cryogenic fluid may be a gas or may be a liquid. In one embodiment where it is a gas, each cryoprobe further has a heat exchanger disposed within the shaft in thermal communication with the conduits of the cryoprobe. In addition, each cryoprobe may include a Joule-Thomson port disposed in the distal end of the shaft in thermal communication with the heat exchanger, with the computer processor additionally controlling operation of each of the Joule-Thomson ports. In one embodiment where the cryogenic fluid is a liquid, the computer processor controls the compressor and flow-control metering valves to provide an initial flow of the liquid under physical conditions near a critical point of a liquid-vapor system for the liquid. Vapor lock associated with freezing of the cryoprobes is thereby avoided. The computer processor may subsequently control the compressor and flow-control metering valves to reduce a pressure of the liquid in the cryoprobes, allowing colder liquid temperatures to be maintained without vapor lock after the initial flow is established. In one instance, a source of warmed gas may be flowed through the conduits as part of an active-thaw procedure.

The compressor may comprise a submersible pump for compressing ambient cryogenic liquids. In one such embodiment, the compressor comprises a heat exchanger to remove heat of compression through heat exchange of the compressed cryogenic liquid with the ambient cryogenic liquids. In another such embodiment, the plurality of cryoprobes are in fluid communication with the submersible pump through respective supply lines; the computer processor is further adapted to set a freeze power of the plurality of cryoprobes by regulating flow through the respective supply lines. In an alternative configuration, the compressor comprises a push-pull bellow system and a linear actuator motor. In one such embodiment, the computer processor is further adapted to control a force exerted by the linear actuator motor to set a pressure of the cryogenic liquid.

In some embodiments, the computer processor may determine the desired flows from predefined imaging parameters. For example, the predefined imaging parameters may correspond to a definition of freeze margins in the body.

In other embodiments, each of the cryoprobes further has a plurality of multifunction electrical wires, with the computer processor being adapted to monitor the operation of the multifunction electrical wires. For instance, the multifunction electrical wires may be used to monitor a temperature, to provide heat, to stimulate a nerve within a living body, to permit spatial localization of the cryoprobes, and the like. In one embodiment, ends of the cryoprobes comprise an electrically insulating material and the computer processor is further adapted to force current between the ends of the cryoprobes to heat intervening portions of the body. In another embodiment, the computer processor is further adapted to initiate injection of a cryosensitizing substance into the body.

The methods of the present invention may be embodied in a computer-readable storage medium having a computer-readable program embodied therein for directing operation of a cryotherapy system such as described above. The computer-readable program includes instructions for operating the cryotherapy system in accordance with the embodiments described above.

BRIEF DESCRIPTION OF THE DRAWINGS

A further understanding of the nature and advantages of the present invention may be realized by reference to the remaining portions of the specification and the drawings wherein like reference numerals are used throughout the several drawings to refer to similar components. In some instances, a sublabel is associated with a reference numeral and follows a hyphen to denote one of multiple similar components. When reference is made to a reference numeral without specification to an existing sublabel, it is intended to refer to all such multiple similar components.

DETAILED DESCRIPTION OF THE INVENTION

1. Introduction: Thermodynamics of Cooling Cycles

As an initial matter, we analyze and compare two methods of cryogenic refrigeration that are currently being used in various cryotherapy tools: a) isoenthalpic expansion cooling (the Joule-Thomson process) from a high-pressure gas (Ar or $N_2$), and b) direct injection of a liquid coolant (liquid $N_2$, hereafter $LN_2$) into the tip of a cryoprobe.

a. Joule-Thomson (JT) Cooling

This refrigeration technique uses a high pressure gas supply (≈6000 psi), a JT expansion jet that cools the tip of the probe, and a small heat exchanger that is mounted inside the cryoprobe. Assuming ideal (perfect) heat exchange between the gas streams, the maximum cooling power of the JT cooling is equal to 1.86 kJ/mol for Ar gas at its boiling temperature (and one atmosphere pressure) $T_{Ar}$=87 K. If nitrogen gas is used, the maximum cooling power is about 1.6 times less i.e. 1.15 kJ/mol.

The main disadvantage of this method is very large gas consumption since the vapor/liquid ratio after expansion is about 2.5. In practice this ratio is considerably larger since the heat exchange between the streams in a small probe is far from being ideal. This provides a limitation on the probe's diameter—in order to achieve a reasonable cooling power, the geometrical impedances for the gas channels in the probe should be sufficient to allow for the adequate amount of gas to be supplied to/from the JT junction.

b. Cooling with Liquid Nitrogen

A direct injection of the liquid coolant into a freeze zone of the cryoprobe appears to be much more effective when compared to JT cooling. For example, to achieve the same cooling power as in the JT process the required molar flow of the liquid coolant can be 3-4 times less (3.5 times for Ar and 4.5 times for $N_2$). Liquid nitrogen is the most commonly used and cheapest cryogenic liquid, and its boiling temperature is about 10 K lower under one atmosphere of pressure than that of argon. Thus, the analysis presented below is for $LN_2$.

Figure 1:
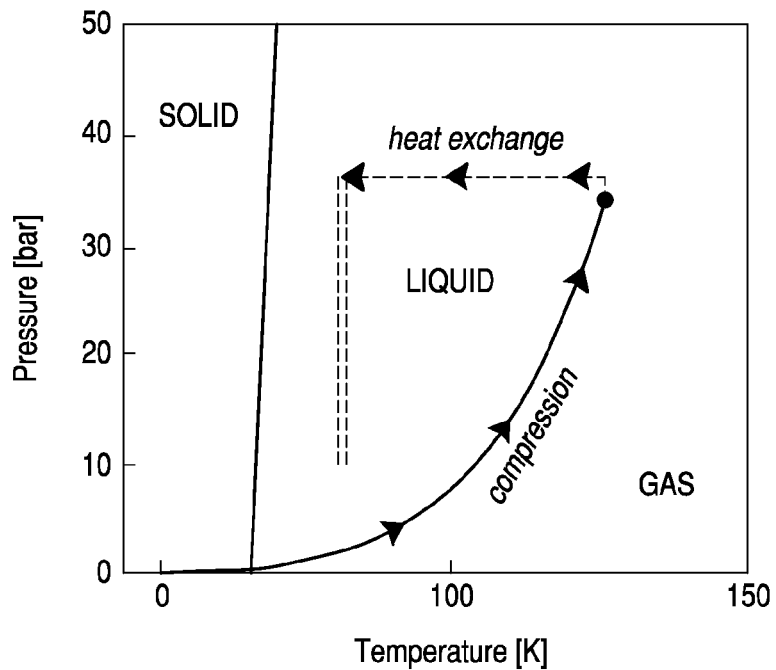
FIG. 1 is a phase diagram illustrating the phase structure of a liquid like $LN_2$.

$LN_2$ encounters vapor lock when standard pressures (1 atm) are considered since the volume expansion from liquid to gas is 171 fold (see molar volume in Table 1 below). The flow of $LN_2$ is thus rapidly blocked, and the flow of the very low density vapor phase at one atmosphere has very poor cooling power, eliminating the potential benefits of $LN_2$ cooling and its low costs. Considering the high pressures for the JT effect and our optimized flow considerations, it then follows that $LN_2$ may also be pressurized to eliminate flow disruption due to marked volume expansion. As the pressure is increased toward the critical point the vapor density increases, greatly reducing the negative impact to the refrigeration system when vapor forms. The critical point for $LN_2$ is reached at ~33.5 atm (Table 1) where the molar volumes are substantially equivalent for liquid and gas. While the fluid temperature has increase from 77K to ~130K (Table 1), a post compression heat exchanger may be used to cool the compressed $LN_2$ to the ambient bath temperature of 77K again. A typical phase diagram for a liquid like $LN_2$ can be seen in FIG. 1, whereby the critical point is noted, along with the projected compression sequence to a cooler operating point. Compression is first used to increase the pressure of $LN_2$ along the liquid-vapor curve; then, the heat exchange with the $LN_2$ bath lowers the compressed liquid temperature to the probe operating point as shown. We use the term 'near critical nitrogen' to refer to liquid nitrogen held near its critical pressure of 33.5 atmospheres.

The only complication to the technical design in this case is the need to thermally isolate the inlet (coolant supply) tube so that the compressed $LN_2$ will arrive at the cryoprobe at a temperature close to 77 K. It is also desirable that the liquid flow not form gaseous bubbles anywhere except possibly at the probe tip under large heat loads, so as not to create a vapor lock condition that limits the cooling power. By operating near the critical point of the liquid-vapor system the vapor phase is much more dense than it would be if operated near atmospheric pressures. This makes the volume expansion of the liquid into the vapor phase much less, and it makes the resulting vapor phase a much more effective coolant.

The design of the $LN_2$ circulation cryoprobe itself becomes significantly simpler in comparison to that of the JT cycle based cryoprobe—both the internal heat exchanger and the JT jet are no longer required. The overall internal structure of the probe can be reduced to a very simple design discussed below in connection with FIG. 5. This simplified design results in lower manufacturing costs for the probe, which is important in markets where the probe is disposed of after each use, or returned for a re-cycling credit. The optimal performance of the probe and its main characteristics can be estimated based on the thermodynamic properties of nitrogen, which are summarized in the Table 1 below.

TABLE 1

Thermodynamic Properties of $LN_2$
Properties of $LN_2$ along liquid/gas equilibrium

| P (atm) | T (K) | Molar Enthalpy | | Molar Volume | | Latent Heat L (J/mol) | $Q_{MAX}$ (J/mol) |
| | | $I_L$ (J/mol) | $I_G$ (J/mol) | $V_L$ (cm³/mol) | $V_G$ (cm³/mol) | | |
|---|---|---|---|---|---|---|---|
| 1 | 77.36 | 3550 | 9100 | 35 | 6000 | 5560 | 5560 |
| 2 | 84 | 3900 | 9150 | 37 | 3200 | 5250 | 5600 |
| 3 | 88 | 4200 | 9250 | 38 | 2300 | 5050 | 5700 |
| 5 | 94 | 4500 | 9350 | 39 | 1600 | 4850 | 5800 |
| 7 | 99 | 4750 | 9400 | 40 | 1000 | 4650 | 5850 |
| 10 | 104 | 5100 | 9450 | 42 | 750 | 4350 | 5900 |
| 15 | 111 | 5500 | 9400 | 45 | 450 | 3900 | 5850 |
| 20 | 116 | 6000 | 9250 | 48 | 320 | 3250 | 5700 |
| 25 | 120 | 6450 | 9100 | 53 | 240 | 2550 | 5500 |
| 30 | 124 | 6950 | 8750 | 60 | 165 | 1850 | 5200 |
| | | | | Critical point | | | |
| 33.5 | 126.15 | 7950 | | 90 | | 0 | 4400 |
| | | | | Overcritical Nitrogen | | | |
| 35 | 130 | 8850 | | 115 | | — | 5000 |

The last column of the table $Q_{MAX}$ is the maximum value of the cooling power that can be achieved in this process assuming that nitrogen is "overcooled" through heat exchange with the ambient $LN_2$ bath at 77.4 K. As we see, under these conditions the cooling power is almost independent of pressure up to approximately 30 bars. Moreover, almost the same level of refrigeration per unit mass flow can be produced in the supercritical regime at the pressure≈35 bar (bottom line in the Table 1). After initially establishing flow with overcritical nitrogen, the $Q_{MAX}$ can still be increased by 18% (5900/5000 J/mol) by dropping the operating pressure to 10-15 atm. Operating at this level still represents a 6% increase in $Q_{MAX}$ (5900/5560) over trying to use $LN_2$ at 1 atm, even if vapor lock could somehow be avoided at this pressure.

It is worth noting that "classical" evaporating cooling (where the cooling effect is due to the latent heat only) is able to provide a comparable cooling power only in the low pressure limit. However, running the cryoprobe in the low pressure regime is difficult because of possible vapor locking. It is much more desirable to design a probe that cools by liquid flow, with little or no evaporation at the cooling tip. By avoiding the huge volume expansion into the vapor phase within the conventional $LN_2$ cooled probe (when the $LN_2$ pressure is near ambient pressure of one atmosphere) it is possible to use a much smaller diameter return flow line from the tip, permitting the overall probe diameter to be reduced greatly without sacrificing freeze power. Under very large heat loads, evaporation will occur at the probe tip, but this will have little adverse consequence on the probe freeze power if the liquid nitrogen pressure is close to the critical pressure. Near the critical pressure the vapor phase density is almost the same as in the liquid phase, reducing adverse effects on the probe freezing power when the vapor phase forms. This is one advantage of operating near the critical pressure. In order to achieve the required cooling power, the flow of the $LN_2$ coolant through the cryoprobe has to be maintained on a reasonably high level. This imposes a restriction on the geometrical sizes of the cryoprobe; an estimation of the flow dynamics follows in the next section.

c. Flow Dynamics

In the following estimates it is assumed that the desired cooling power of the probe is 25 W. From Table 1 we find that in an evaporative $LN_2$ refrigerator this cooling power corresponds to a flow rate 0.005 mol/s. This value is used in the calculations below.

Regrettably, the available nitrogen viscosity data is incomplete. The known values are summarized in the Table 2 below:

TABLE 2

Viscosity of gaseous and liquid nitrogen at different temperatures

| T (K) | Viscosity, $10^{-6}$ (Pa · s) | | |
| | Gas at 1 atm | Gas at 25 atm | Liquid $N_2$ |
|---|---|---|---|
| 80 | 5.4 | 130 | ≈150 |
| 90 | 6.3 | 91 | 110 |
| 100 | 7.0 | 72.8 | 90 |
| 110 | 7.4 | 55.6 | 65 |
| 120 | 8.3 | 38.5 | — |
| 130 | 8.9 | 10.6 | — |

(i) Reynolds Numbers

The corresponding Reynolds numbers (R) can be estimated using the following equation:

$$R = \frac{\rho v d}{\eta} = \frac{4\rho \dot{V}}{\pi \eta d} = \frac{4}{\pi} \frac{\dot{m}}{\eta d}$$

where ρ is the density, v is the flow velocity, V is the corresponding volumetric flow rate, and m=ρ V is the mass flow rate. Numerically, assuming the flow rate of 0.005 mol/s and d=0.5 mm, we obtain:

$$R = \frac{4}{\pi} \frac{28 \cdot 10^{-3} \cdot 5 \cdot 10^{-3}}{5 \cdot 10^{-4} \eta} = \frac{0.356}{\eta [\text{Pa} \cdot s]}$$

(ii) Pressure Drop
1. Case of the Liquid Flow

Assuming initially that in liquid $\eta = 10^{-4}$ Pa·s (some average value) we obtain that for a 0.5 mm capillary the Reynolds number has to be on the order of 3500 (1800 for a 1 mm capillary or 6000 for a 0.3 mm one). This indicates that the flow is in the transition zone (laminar to turbulent) and in this case the Colebrook equation of an ideally smooth circular pipe is used to estimate the pressure drop $\Delta p$. The resistance coefficient K in this formula can be estimated as $K=fl/d\approx20$, where $f=4\cdot10^{-2}$ is the friction factor, $l=25$ cm is the length of the capillary and $d=0.5$ mm is its inner diameter. Then the pressure drop $\Delta p$ can be defined as $$\Delta p = K\frac{\rho v^2}{2}$$

taking into consideration that $$\rho v = \frac{4}{\pi d^2}\dot{m}$$

we finally obtain $$\Delta p = K\frac{8}{\pi^2 d^4}\dot{m}\dot{V}$$

The average molar volume of the liquid is $v_L\approx40$ cm³/mol. This multiplied by our optimal circulation rate of 0.005 mol/s results in $\dot{V}\approx0.2$ cm³/s. Finally, from the above equation and with d=0.5 mm, we obtain $\Delta p_{0.5}\approx7260$ Pa. Similarly, for d=0.3 mm we obtain f=0.037, K=30.8, and $\Delta p_{0.3}=8.7\cdot10^4$ Pa. Hence at 0.3 mm we suffer a pressure drop of about 87% of an atmosphere, which is manageable in the engineered support system.

The probability of the vapor lock for this flow can be estimated using so called Weber number that is the ratio of the kinetic energy of the flow to the characteristic surface tension energy. The average velocity of the liquid is given by $v=4\dot{V}/\pi d^2 \approx 1$ m/s for a 0.5 mm capillary. Surface tension of the liquid nitrogen at 90 K (average) is equal to $\sigma=6\cdot10^{-3}$ N/m. Hence the Weber number becomes $W_{0.5}=\rho v^2 d/\sigma\approx600$ indicative of a very low probability of a vapor lock. Correspondingly, $W_{0.3}=270$.

2. Case of the Gaseous Return Flow

Assuming the circulation rate $5\cdot10^{-3}$ mol/s, the volumetric flow rate and the corresponding flow velocity for saturated $N_2$ vapor in the 0.5 mm ID capillary are calculated and presented in the Table 3 below:

TABLE 3

Volumetric flow rate and flow velocity

| | P (atm) | | | | | | | | |
|---|---|---|---|---|---|---|---|---|---|
| | 1 | 2 | 3 | 5 | 7 | 10 | 15 | 20 | 25 | 30 |
| V (cm³/s) | 30 | 16 | 11.5 | 8.0 | 5.0 | 3.8 | 2.2 | 1.6 | 1.2 | 0.82 |
| v (m/s) | 153 | 81.5 | 58.6 | 40.7 | 25.5 | 19.4 | 11.2 | 8.2 | 6.1 | 4.2 |

Note that the flow velocities at the low pressure end appear to be very close to the sound velocity in nitrogen at these temperatures—at 77K the speed of sound is $\approx180$ m/s and it slightly raises with temperature reaching 200 m/s at 100K. Thus, the applicability of the incompressible liquid approximation used in our analysis is restricted to the region of relatively high pressures (in practice>5 bars).

The Reynolds numbers can be estimated using the equation in the previous subsection, although we need to interpolate the viscosity data. That gives the following estimates for a 0.5 mm capillary: $R_{1\text{-}2\ bar}\approx6\cdot10^4$, $R_{3\text{-}5\ bar}\approx5\cdot10^4$, $R_{15\text{-}25\ bar}\approx1\cdot10^4$. An estimation for the pressure drop is more difficult than in the case of liquid flow and is done in the limit of an incompressible gas. Then, taking $R=5\cdot10^4$, f=0.021, and the friction coefficient $K=fl/d\approx10$, we obtain $\Delta p$ $2.2\cdot10^5$ Pa, which is about 2.2 atmospheres. Again, the pressure is manageable with embodiments of the invention described herein.

(iii) Volume of $LN_2$ Required

The problems with prior high volumes of $LN_2$ usage in the other cryosystems have also been overcome. Namely, such units would use up the 50 liters of supercooled $LN_2$ within a "slush" dewar well before even a single large case was over. This required a time consuming "regeneration" cycle of re-cooling the $LN_2$ within the return dewar to re-supply the slush dewar. Such systems pressurized $LN_2$ to only 5 atmospheres, which was not adequate to obtain the near critical properties discussed above. Then the compressed $LN_2$ was supercooled to about 63 K through heat exchange to a $LN_2$ bath in a 'slush dewar' that was held at a vacuum of about 98 torr to reach the triple point on the liquid nitrogen phase diagram. This supercooling of the $LN_2$ at 5 atmospheres to the temperature of the slush dewar provided only small additional cooling power than would be obtained if the compressed liquid nitrogen had been cooled to 77K through heat exchange with a liquid nitrogen bath at one atmosphere. Hence the engineering complexity of the slush dewar did not justify the very minimal improvement in cooling capacity of their liquid nitrogen flow following heat exchange with the slush dewar. As displayed in Table 1, liquid nitrogen at 25 atmospheres has essentially the same cooling power, Qmax, as does liquid nitrogen at its one atmosphere boiling point, but at 25 bar the vapor phase density is more than one fifth of the liquid density, and over thirty times more dense than the vapor phase under one atmosphere of pressure. Hence flowing liquid nitrogen at 25 bar will provide the full advantages of liquid nitrogen flow cooling at lower pressures without the adverse effects of cooling system failure due to vapor lock at the lower pressures.

In the prototype small probe tested within this application we found that 0.02 STP liter per second of nitrogen was required to produce full cooling power. This flow rate corresponds to one liquid liter per hour of $LN_2$ under its 'ambient' conditions (at its boiling point under one atmosphere of pressure). This liquid must be compressed to pressures near its critical point, and the heat of compression from one atmosphere to this pressure must be taken away by evaporation of the surrounding liquid nitrogen bath which cools the compressed $LN_2$ back to 77 K following its compression to 30 atmospheres. This removal of the heat of compression to 30 bar corresponds to an additional evaporation of 0.81 liters per hour of $LN_2$ under ambient conditions, as discussed below.

In summary, 36 W of additional cooling are required to remove an assumed heat of compression from the 0.2 standard liters per second (SLPS @ 1 atm.) flow rate per probe. This means that each probe will require 0.8 liters of $LN_2$ per hour to remove the heat of compression. This adds to the direct probe consumption of one liter per hour to give a total system $LN_2$ consumption of 1.8 liter per hour per probe of $LN_2$ for this fully self-contained system configuration running full-out. At lower flow rates the consumption will be much less, but we have therefore assumed ~2 liters of $LN_2$ per probe per hour as the absolute worst case estimate.

TABLE 4

Physical properties of $LN_2$

From Jacobsen and Stewart, $N_2$ tables
J. Phys. Chem. Ref. Data 2, 757 (1973)

|  | mol/l | g/cm3 | T(K) | S(J/mol/K) | H (J/mole) |
|---|---|---|---|---|---|
| density at SVP and 77 K | 28.865 | 0.808607 | 77.347 | 79.53 | −3401.75 |
| density at SVP = 30.574 bar | 16.388 | 0.459084 | 124 |  | −13.85 |
| density at 30 bar and 78 K | 28.998 | 0.812333 | 78 | 79.45 | −3307.3 |

| Once at 30 bar and 78 K: | Cp (J/mol/K) | | |
|---|---|---|---|
|  | 56.82 | | |
| Heat of Compression = | T ΔS = | 6.24 J/mol | |
| Compression factor = | 1.004608 | | |
| Heat of compression = | 6.24 | J/mol | |
|  | 180.9475 | J/l | |
|  | 36.1895 | W/(0.2 l/s) | |
| Latent Heat (77 K/1 atm) = | 199 | J/g | |
|  | 160.9128 | J/cm³ | |
| So, 36 W boils | 0.224901 | cm³/s | |
|  | 809.6451 | cm³/hr = | 0.81 l/hr | d. Comparison

For a small diameter cryoprobe it may be more advantageous to use $LN_2$ in the freeze zone as compared to the JT-cooling cycle—the flow rate required to provide the same cooling power is much less. This is especially true since the flow velocities in the gas phase appear to be already very close to the sound velocity in the return line assuming a JT process. This problem is alleviated by using liquid nitrogen.

A temperature of the compressed liquid nitrogen has to be supercooled close to its boiling temperature under one atmosphere (77K); in this case the increase in working pressure does not result in a decrease of cooling power up to the pressures almost as high as the critical pressure, as displayed in Table 1.

For a designed cooling power 25 W (or flow rate 5 mmol/s) the acceptable diameters of the inlet/outlet capillaries can be estimated assuming reasonable pressure difference on its ends and the flow velocities. To deliver this cooling power in practice the inlet capillary may be larger than about 0.3 mm (ID) and the outlet capillary may be larger than about 0.5 mm (ID). Thus the outer diameter of the vacuum jacketed cryoprobe may be made as small as about 1.2 mm. For a JT-based probe the probe is generally at least 2.5 mm in diameter to provide a comparable cooling power. As described earlier, this greater diameter in the JT probe is used to support the counterflow heat exchanger without exceeding the speed of sound in the return gas flow line.

A very small diameter cryoprobe can be built if supercritical, or near critical, nitrogen is used in its cooling cycle. This may involve working at 29-35 bars of pressure and temperatures 78-80K. The cooling power for this cycle rises with temperature and for 0.005 mol/s flow rate reaches 25 W at 130K.

2. Cryotherapy System a. Overview

This disclosure details several self-contained cryotherapy probe designs for both liquid and gas-based systems, where "self-contained" is intended to refer to open or closed-loop configurations that permit sustained use without repeated refilling or exchange of tanks. The optimal physics-based probe and system configurations are described for various embodiments which address the prior problem of vapor-locking with liquid based systems and optimized flow considerations to allow more efficient and/or closed-loop gas-based systems.

Methods, cryoprobe device(s), and cryotherapy systems for delivering percutaneous cryosurgery and cryotherapy that overcome deficiencies of the prior art are now described. The process can either use a number of small isenthalpic cooling probes which have greater freeze capacity per unit size (and gas flow rate), or may utilize a new form of delivery of liquid cryogens (i.e., $LN_2$) that avoids vapor-lock by compressing the liquid to its near-critical point. These probes may clinically achieve increased freeze capacity without increasing engineering complexity or cost, yet allowing significant operator-interactive control as desired. The cryoprobe design may achieve increased thermodynamic and/or hydrodynamic efficiency so that the reduced size and cost of the engineered system are achieved in an associated closed-cycle system for gas-based systems, or a self-contained system for the delivery of near-critical fluids. A closed-cycle system design for gases, or an efficient near-critical liquid system, reduces the operational complexity by being fully self-contained, so compressed gas tank changes or lengthy regenerative/re-filling cycles are not required during extended medical procedures. Once multiple probes are inserted their position within the intended freeze zone is determined using an imaging modality, such as CT, MRI or ultrasound. The flow of the closed-cycle gas through each of the multiple probes is adjusted automatically to sculpt the freeze zone to match the intended freeze region specified by the physician. The probe construction has thus been matched to programmable, interactive, self-contained system operation. A new thermocouple design allows probe tip measurement in even smaller probes (i.e., <2 mm), can facilitate probe heating for thawing, simplifies construction and lowers manufacturing costs. The injection ports of the cryoprobe(s), or separate multiprong injection probe system, also allows modulation of the freeze parameters, or extent of freeze, within the adjacent tissues.

As illustrated above, the principles of vapor lock effectively limit the cooling capacity of conventional flow liquid-nitrogen systems. For example, U.S. Pat. Nos. 5,254,116 and 5,334,181 described an approach that increased cooling rates of probes to less than a minute and allowed probe temperatures around −200C, which was lower than the boiling temperature of $LN_2$ under ambient conditions (−197C). However, this required a complex system that sub-cooled $LN_2$ to ~−200-208C via two large dewars that supplied and recycled the $LN_2$, one of which (the 'slush dewar') had to be maintained at a reduced pressure of approximately 100 torr. The probe design allowed $N_2$ gas to escape via tiny holes from the supply line to the return line to allow continuous flow of $LN_2$, even during the ~170-fold gaseous expansion of $LN_2$ within the probe tip that caused evaporative cooling of the biological tissues adjacent to the conductive metal of the probe tip. In addition to minimizing vapor-lock, the concentric position of the supply line inside the return line also allowed some escaping $LN_2$ to create cooling of the returning $LN_2$ for capture in the receptacle dewar. However, this system was quite large for most operating rooms, let alone more crowded imaging suites (e.g., CT), and wasn't efficient in operating procedures or $LN_2$ consumption. The sub-cooling process took additional preparation time after the machine was set-up and the high volume flow frequently emptied the "slush" dewar during large cases, requiring another time-consuming "regenerative" cycle to re-fill the slush dewar. The time of nearly a minute for each probe to be frozen stuck and several minutes to thaw to become free from the surrounding tissue, so that the probe may be moved, made the system more frustrating for time-conscious operating room or imaging suites.

The embodiments described herein provide for improvements in thermodynamic and hydrodynamic efficiencies for gas-based probes and allows better consideration of future closed-cycle systems using mixed gases. Our observation of properties of the transition of compressed gas to the liquid state, at and beyond the JT port of the expansion chamber, also suggested certain concepts incorporated in some embodiments for avoiding flow problems with liquid nitrogen as it expanded to a gaseous state within the expansion chamber of the tip.

Prior liquid nitrogen based ($LN_2$) probe cooling systems operated near or slightly above atmospheric pressure, where the liquid is 170 times more dense than its vapor at the same temperature. This is far from ideal, since if heat absorbed by the flowing $LN_2$ cryogen exceeds a threshold level, then the vapor phase of $LN_2$ will form in an uncontrollable way within the liquid flow and this vapor phase will displace suddenly a much larger volume, equal to this same factor of 170 times the volume of the liquid evaporated (see Section 1 above). This fills the probe tubing with a large quantity of gas that is far less efficient at removing heat from the surrounding tissue through the probe wall. The excess heat from the tissue around the probe that now can not be carried away by circulating liquid causes more and more evaporation of the $LN_2$ in the probe until the entire probe is filled with vapor. This vapor lock is a significant limitation to the reliable operation of $LN_2$ systems at low pressure. Similar vapor lock problems have been a significant limitation to the use of $LN_2$ flow cooling to support long-wavelength infrared sensors on the image planes of systems on satellites, aircraft, and other remote platforms for imaging various objects of interest, and a significant limitation in cooling many other devices by $LN_2$ circulation.

The threshold heating power ($Q_{MAX}$ in Table 1 times the molar flow rate) to create the vapor phase in the probe depends on both the rate of $LN_2$ flow through the probe, and the pressure of the $LN_2$ within the flow. If L is the latent heat per unit volume of the $LN_2$, and H is the amount of heat energy necessary to warm the $LN_2$ to the temperature where vapor may form, then this threshold heating power level to create vapor in the probe, in watts, is simply (L+H) dV/dt, where dV/dt is the volume flow rate of $LN_2$ through the probe.

As discussed by many authors [see, for example H. Eugene Stanley, Introduction to Phase Transitions and Critical Phenomena (Oxford University Press, 1971)], as the pressure is increased the difference in the densities between the liquid and vapor phases becomes less and less, until at the critical point pressure and temperature the liquid and vapor have the exact same density. Hence, as the pressure of the circulating $LN_2$ cryogen is increased, the consequence of vapor formation on the proper operation of the probe becomes far less significant, since the volume expansion of the vapor phase beyond the original liquid volume evaporated becomes less as the pressure is increased, until it becomes zero at the critical point. Furthermore, the much higher density of the vapor phase near the critical point makes it far more efficient at circulation cooling than the vapor phase far from the critical point. Hence if the $LN_2$ is circulated at exactly its critical point pressure and temperature, then the catastrophic failure of probe freezing associated with vapor lock, which occurs at lower working pressures, physically can not occur. This results in a vastly more reliable and hence easier to use cryogenic freeze cycle.

As discussed in Section 1 above, the Weber Number, which is the ratio of the kinetic energy of flow to the surface energy of the liquid-vapor interface, is a good indicator of the likelihood of vapor lock. When the Weber number is large, then the likelihood of vapor formation is small. Hence it is possible to design the circulation system to operate away from the critical point conditions, where vapor lock is impossible, to lower pressures where vapor formation is very improbable, provided that the Weber number is sufficiently large. This implies that the optimal control cycle for the $LN_2$ flow system may start at high pressure (critical or near-critical conditions) and then relax to lower pressures as the $LN_2$ flow is well established, provided that the Weber Number remains large. At a given sub-critical operating pressure the Weber Number may be increased by increasing the flow, however this option is less desirable because the increased flow expends the $LN_2$ more rapidly, resulting in more frequent refills and hence in a more complex engineered system to cool the cryoprobe. As discussed above, near the critical point two-phase flow remains efficient in cooling applications, since the vapor density is large. This higher pressure operation, near the critical pressure, makes the consequence of vapor formation much less detrimental to the proper freeze power of the probe.

Once the liquid has been compressed to elevated pressures near its critical pressure it may be passed through a heat exchanger with the ambient pressure $LN_2$ bath in order to over-cool the compressed liquid, resulting in a greater cooling power per unit volume of the flowing cryogen, as discussed in Section 1 above.

Embodiments of the invention provide a novel method of circulating $LN_2$ cooling with the $LN_2$ held near its critical point to avoid vapor lock (see discussion of FIGS. 5-7 below). This method of cooling, called Near Critical Nitrogen (NCN) cooling, is applied below to the optimization of the freeze performance of very small probes (see discussion of FIG. 5 below), where more conventional cooling techniques based on the JT process become impractical, as discussed in Section 1 above. Hence this NCN cooling process makes it possible to reduce the diameter of cylindrical freeze probes to less than 1.5 mm, and to vastly reduce the complexity and size of the engineered system into a single, self-contained unit with no external pressure tanks (see discussion of FIGS. 6A-E below).

While this improved method of cooling is described herein for application to probes for cryosurgery (see discussion of FIG. 7 below), it has very broad applicability to all cryogenic cooling applications involving a flow of liquid cryogen. More generally, the methods described herein may be used to cool other devices with any cryogen flow operating near its critical point. These devices may include sensors within image plane arrays for remote sensing applications, superconducting wires and cables, and all other devices requiring cryogenic support. Other cryogens of interest using this technique include and liquefied gas, including argon, neon, xenon, helium, hydrogen, and oxygen, to name a few. These are single component flowing liquid-vapor systems. Mixtures of substances in flowing liquid vapor systems may also be used in this way, such as flowing hydrocarbon gas mixtures, provided that their critical point pressures and temperatures are readily obtained within the engineered cooling or liquid-gas processing system.

In addition, certain prior-art cryoprobe design is limited by not actually placing thermocouples within the active cryogen chamber within the tip of the cryoprobes themselves in order to avoid manufacturing complexity, etc. For both prior $LN_2$ and prior gas-based systems, thermocouples are more generally placed in or near the return line such that the thermocouple read-outs are not the actual, lowest tip temperature. For example, assuming perfect heat transfer from the JT expansion chamber, tip temperatures for Argon should be close to its boiling point of 87K (or ~−183C). However, even the most recently available probes rarely display probe temperatures below −150C. If conventional cryoprobes could be miniaturized to even smaller dimensions (i.e., <2 mm), specialized engineering efforts to place the thermocouples at the tip would increase the price of the cryoprobe beyond their already costly levels (~$500-1500). The thermal anchoring of small thermocouples is an additional concern, since these typical copper-constantan thermocouples would need to be mounted within the vacuum space of the shaft but thermally anchored to the cryogenic tip of the probe. Alternatively, the thermocouple may be placed in the flow channel directly; however, this may require a hermetic feed-through for the wires, driving up cost. In new small probe designs this would require that the thermocouple be no larger than about 100 microns along its largest dimension, placing a demanding and expensive limitation on the cryoprobe assembly technique. The embodiments of the invention discussed herein permit accurate, rapid resistance thermometry in very small cryoprobe tips, as well as in adjacent probes, while reducing costs well below current thermocouple measurement systems ($35-124) used in cryoprobes today. The use of resistance thermometry is highlighted here to demonstrate its remarkable flexibility in allowing very small probe design, multiple functions (i.e., thermometry, nerve stimulation and probe heating) and yet reducing production costs for an otherwise disposable cryoprobe.

b. Cryoprobe and Cryosystem Designs

Figure 2:
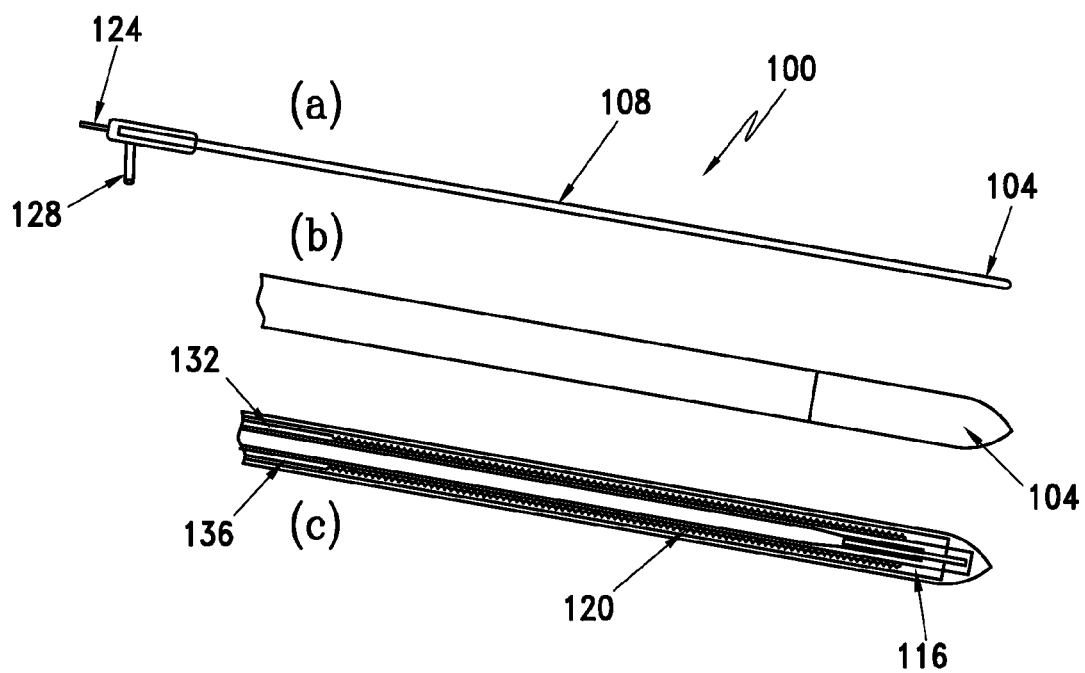
FIG. 2 is a schematic illustration of an embodiment of a gas-based cryoprobe in accordance with an embodiment of the invention.

A structure for a cryoprobe according to an embodiment of the invention is provided in FIG. 2. Part (a) of FIG. 2 provides a perspective view of the cryoprobe 100, which includes a shaft 108 having a metal tip 104. In one embodiment, the metal tip comprises a copper tip with gold plating. Gas is flowed through the cryoprobe 100 through a high-pressure inlet 124 and returns from a low-pressure outlet 128. Part (b) provides an expanded view of a distal end of the cryoprobe showing the metal tip 104 more clearly. A cutaway view of the tip is shown in part (c) of FIG. 2, illustrating a supply conduit 136 that is provided in fluid communication with the high-pressure inlet 124 and a return conduit 132 that is provided in fluid communication with the low-pressure outlet 128. A heat exchanger 120 acts precools the incoming high-pressure gas along the supply conduit 136 with the outgoing gas flowing along the return conduit 132, allowing lower temperatures to be obtained. A Joule-Thomson junction 116 is provided in fluid communication with the heat exchanger. As discussed further below, the shaft 108 may be vacuum jacketed from the inner heat exchanger 120 to ensure that the shaft 108 remains at ambient temperature.

Figure 3:
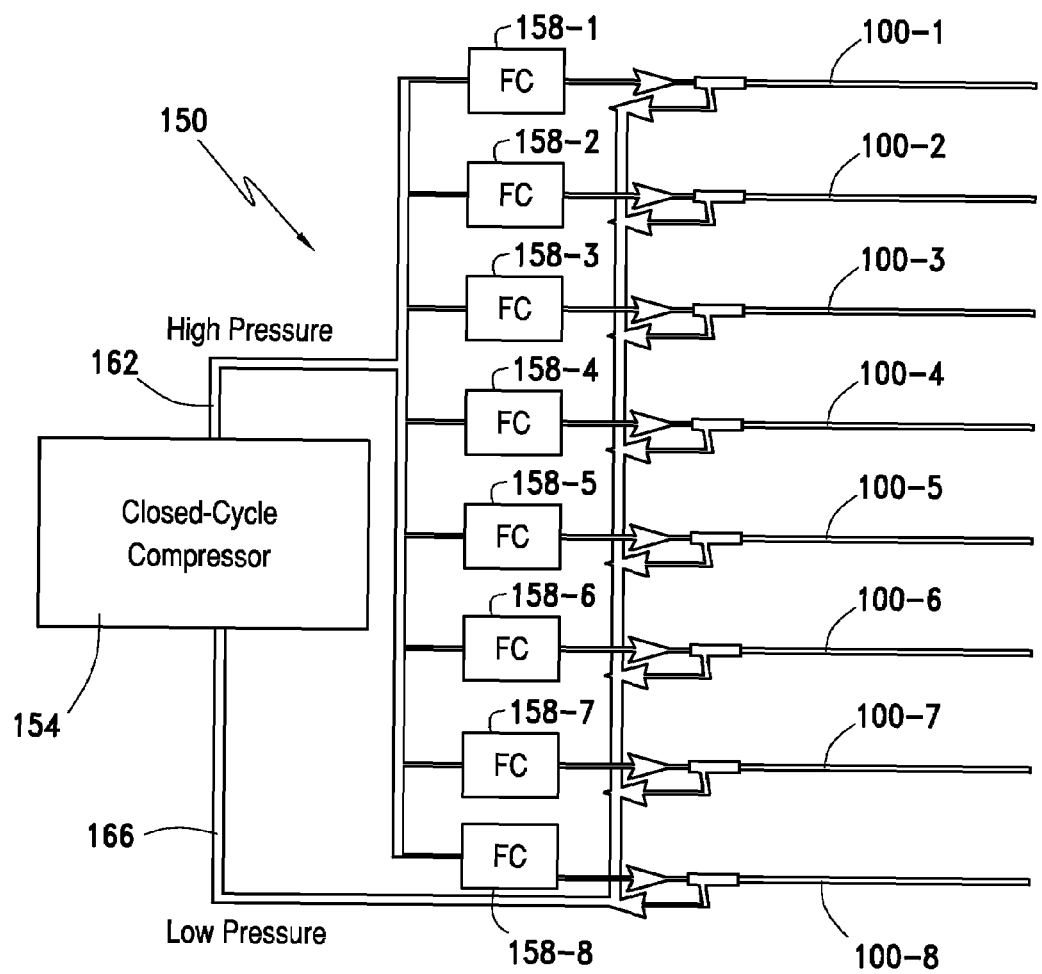
FIG. 3 is a schematic illustration of a gas-based cryosystem that uses the gas-based cryoprobe of FIG. 2 according to one embodiment of the invention.

The cryoprobes of FIG. 2 may be used as part of a gas-based cryosystem, an example of which is shown schematically in FIG. 3. The system is denoted generally by reference numeral 150 and is shown in the figure to accommodate eight cryoprobes 100, although any number of cryoprobes 100 may more generally be accommodated. Gas flow through the cryoprobes 100 is regulated with a closed-cycle compressor 154 and a plurality of flow regulators 158, each of which is provided in fluid communication with the high-pressure inlet of a corresponding one of the cryoprobes 100. The low-pressure outlets of the cryoprobes 100 are provided in fluid communication with the closed-cycle compressor 154 through conduit 166 and the flow controllers 158 at the high-pressure inlets are provided in fluid communication with the closed-cycle compressor 154 through conduit 162. The arrangement thus provides a closed flow system for the gas, with flows through individual cryoprobes 100 being regulated individually with states of the flow controllers 158.

Figure 4:
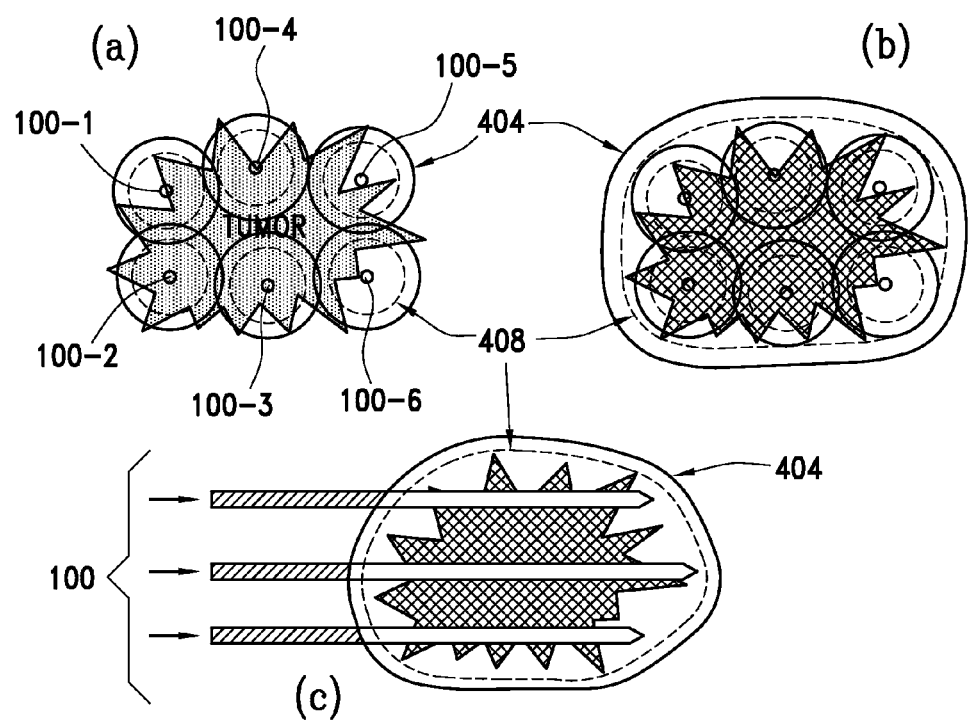
FIG. 4 is a schematic illustration of a tumor treatment using six cryoprobes in accordance with an embodiment of the invention.

FIG. 4 provides a schematic illustration of a tumor treatment that uses six cryoprobes 100 in accordance with an embodiment of the invention. The probes 100 are separately driven and computer monitored using image guidance to attain potentially differing iceball sizes as needed, ensuring adequate tumor coverage. Part (a) of FIG. 4 provides an axial view that illustrates a suitable placement of the six probes 100 in treating an irregularly shaped tumor. Each probe may produce about 2.5-cm diameter of visible ice (i.e. 0° C.) on ultrasound or x-ray computed tomography. Curves 404 denote a boundary of the visible 0° C. ice-line region. A boundary of cytotoxic, or lethal (i.e. less than about −40° C.), ice is denoted with curves 408, which is generally about 3-5 mm behind the leading edge of the visible ice.

The cryoprobes 100 may thus be placed to approximate the irregular contours of the tumor, with each probe being driven only to the extent needed to provide lethal coverage. The freeze length may be about 5-cm of lethal ice. After about a ten-minute freeze cycle, the ice reaches its maximum freeze intensity, as seen in the full-ice axial and sagittal images in parts (b) and (c) of FIG. 4, in which the contour of the −40° C. line covers all tumor margins. Neighboring normal tissue is thus spared by driving the probes 100 only to the extent required to provide thorough tumor coverage, effectively sculpting the ice.

Figure 5:
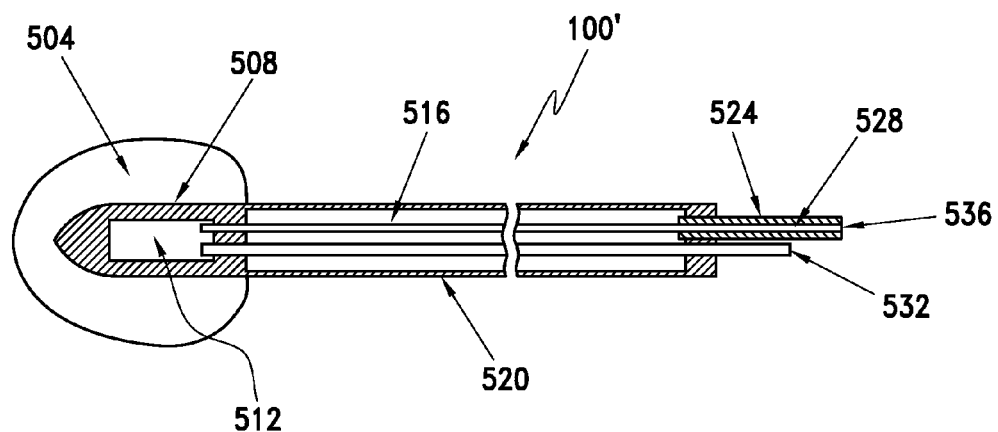
FIG. 5 is a schematic illustration of a cryoprobe in an embodiment of the invention using a liquid-nitrogen circulation cycle.

A liquid-based cryoprobe is illustrated for an alternative embodiment in FIG. 5. In this embodiment, the cryoprobe 100' uses a liquid nitrogen circulation cycle. Liquid nitrogen may be supplied to the cryoprobe at inlet 536 through inlet capillary 528, which is thermally insulated with insulation 524. The liquid flows to an evaporation and exchange zone 512 at the tip 508 of the probe 100' to produce an exterior freeze zone 504. An outlet capillary 532 provides a return flow path for the liquid nitrogen. The inlet and outlet capillaries are housed within a shield 520 that encapsulates an interior vacuum.

Figure 6A:
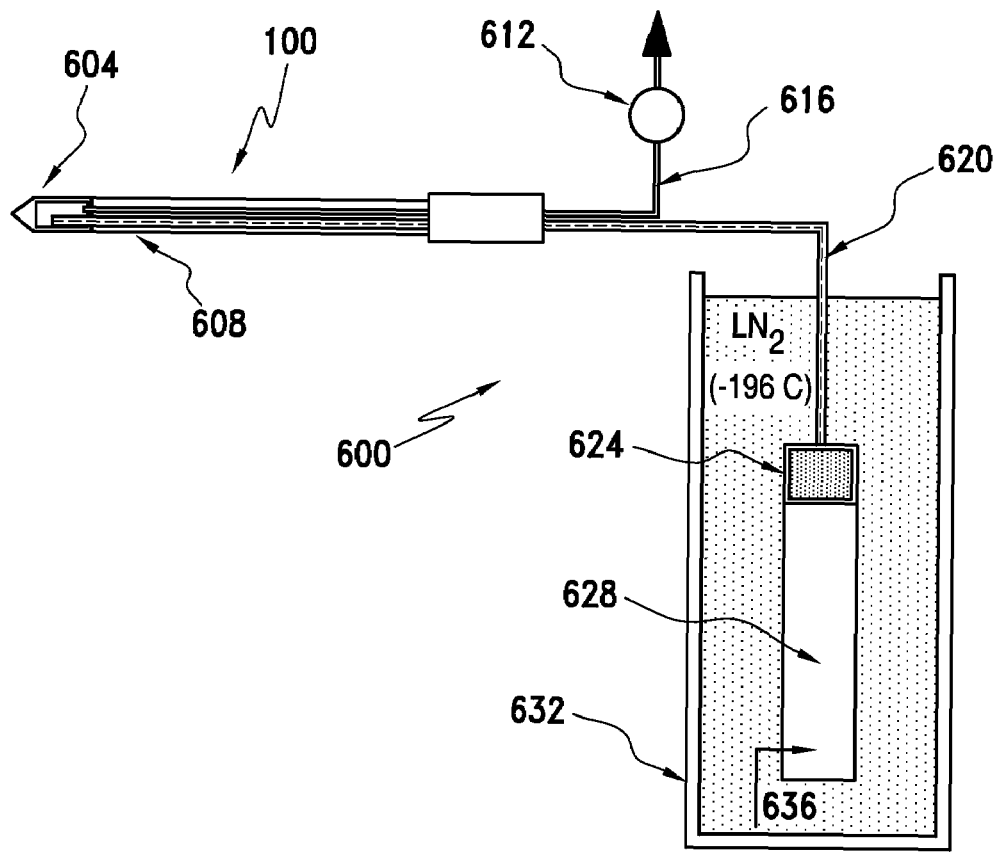
FIG. 6A provides a schematic view of a cryoprobe and simplified near-critical system according to an embodiment of the invention.

FIG. 6A provides a schematic view of a system 600 with which the cryoprobe 100 may be used in some embodiments. A simplified version of the cryoprobe is shown as comprising a probe tip 604 and a vacuum jacket 608, although the probe 100 will have additional features such as described above.

The liquid nitrogen is held within a storage vessel 632 and is supplied through an inlet 636 to a cryogenic compressor 628. A heat exchanger and pressure controller 624 acts to supply the liquid nitrogen to the probe 100 through a supply line 620 and to stabilize pressures within the probe 100. The supply line 620 may be disposed within a vacuum jacket between the heat exchanger/pressure controller and probe 100. Flow is regulated at the output of the cryoprobe 100 with a flow controller 612, allowing gaseous nitrogen discharge.

Figure 6B:
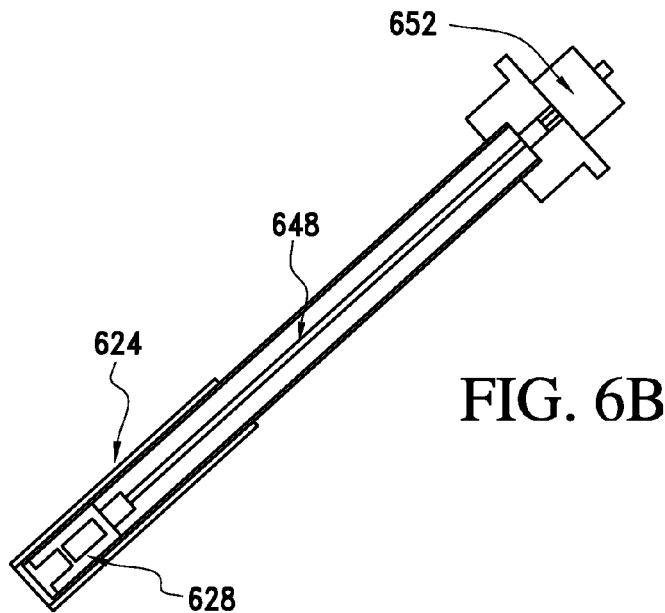
FIGS. 6B and 6C provide illustrations of a compressor for $LN_2$ systems used in embodiments of the invention.
Figure 6C:
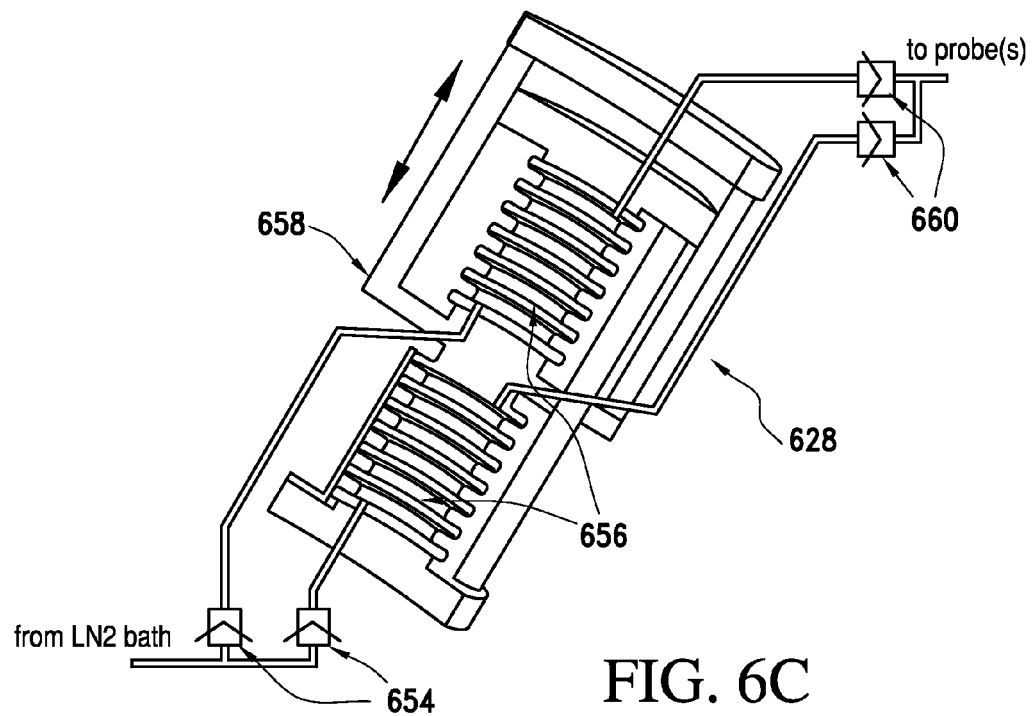

FIGS. 6B and 6C provide schematic illustrations of the cryogenic compressor 628 in one embodiment. It comprises a pair of bellows 656 driven by a linear motor driver 652 along a shaft 648 that separates at room temperature at the top of the liquid-nitrogen dewar from the bellows assembly, which is submersed within the liquid nitrogen. The bellows assembly 656 is arranged such that when the linear motor 652 compresses one bellow assembly in a particular direction of motion, it elongates the other. The bellow being compressed is actuated with a force adequate to produce a pressure within the bellow within the range of 10-33.5 bar, with the compression force precisely controlled by the linear actuator motor 652, which in one embodiment may be a synchronous stepper motor. The bellow being compressed creates a flow of liquid nitrogen out of the bellows 656 and through a check valve 660 that opens only when the pressure within the bellow exceeds the pressure within the heat exchanger 624 (inner cooler) and hence within the cryoprobe supply line. During this compression phase, the other bellow is being elongated, creating a sub-ambient pressure within the elongated bellow. This sub-ambient pressure causes the check valve 654 to the ambient bath to open, drawing in the ambient $LN_2$ into the elongating bellow. The expansion and contraction of the bellows 656 are accommodated by a moveable stage 658.

Once the linear actuator motor 652 reaches the end of its travel in a particular direction, it is rapidly reversed by the motor controller, resulting in the reversal of the functions of the compressed and elongated bellows. Hence, this single linear actuator motor 652 continuously travels back and forth during a freeze procedure, supplying high-pressure nitrogen to the freeze probe through the heat exchanger 624 (inner cooler) with the bath. The pressure generated may be set by the computer controlling the motor actuation force. While the pressure is set and controlled by the actuator motor, the flow rate through each probe is set by the computer adjustable flow impedance at the exhaust line on each probe. This permits the inlet supply lines of multiple probes to be connected to a single submersible $LN_2$ pump and heat exchanger (inner cooler) assembly described herein, with the freeze power of each probe being set independently through computer control of the flow regulator on each probe's exhaust line. The computer controlled flow impedance on the exhaust line of each probe generally creates the largest impedance to flow within the probe assembly. This permits the computer system and operator to sculpt the ice ball by independently controlling the cooling power of each probe with a single common supply of compressed $LN_2$ from the submersible compressor described herein. Furthermore, the push/pull configuration of the bellows described herein permits the submersible pump to operate continuously without flow interruption on a single linear actuator motor, greatly reducing the cost of the submersible pressure actuator. Since the $LN_2$ is virtually incompressible to pressures up to 35 bar, the pressure may be changed rapidly by simply changing the actuation force from the motor. Due to the incompressibility of the $LN_2$, no high pressure reservoir is required in this application.

Figure 6D:
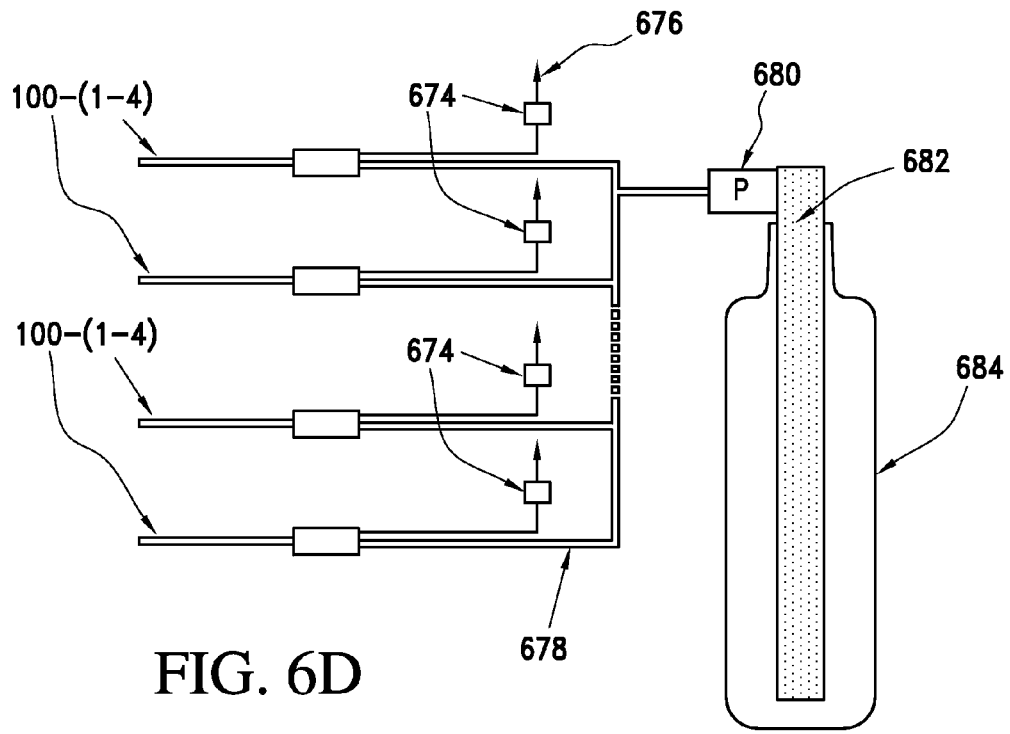
FIG. 6D provides an illustration of one embodiment of a $LN_2$ cryotherapy system suitable for tumor-ablation applications.
Figure 6E:
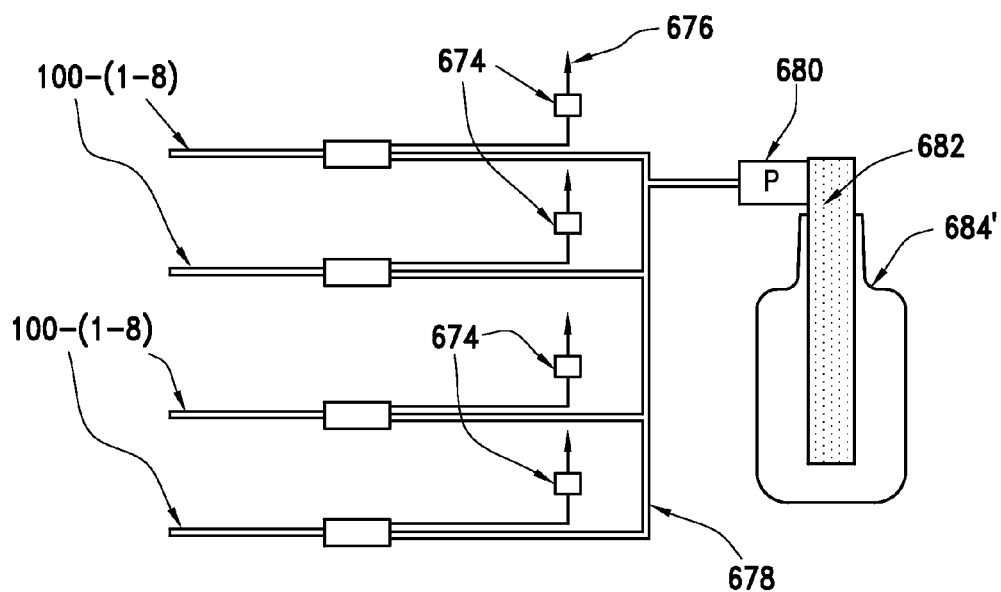
FIG. 6E provides an illustration of one embodiment of a $LN_2$ cryotherapy system suitable for nerve/pain applications.

FIGS. 6D and 6E provide similar schematic illustration of how different configurations of the general structure for the cryotherapy system may accommodate different applications. Both embodiments shown have a plurality of cryoprobes 100 provided in fluid communication with a storage vessel 684 or 684' through compressed $LN_2$ lines 678, a pressure controller 680, and a $LN_2$ compressor 682; flows are controlled with flow controllers 674 and provide a nitrogen discharge 676. In the embodiment shown in FIG. 6D, eight cryoprobes 100-(1-8) may be accommodated for tumor-ablation applications, with a large storage vessel 684 holding about 25-100 liters of $LN_2$ for sustained use of multiple freezes, or several cases during a time period. For example, a full day's activity could have approximately two hours total running time for all eight probes running at 100% capacity, with a ~30 W capacity of a ~2 mm probe. In the embodiment of FIG. 6E, which may be suitable for nerve/pain applications, the number of cryoprobes 100 may be smaller, using about four cryoprobes 100, with a smaller $LN_2$ storage vessel 684' that holds about 5-15 liters. Such a storage capacity is sufficient for sustained use of several cases for a full day's activity, with about two hours total running time for all four probes running at 100% with a ~10 W capacity of a ~1 mm probe.

Figure 7:
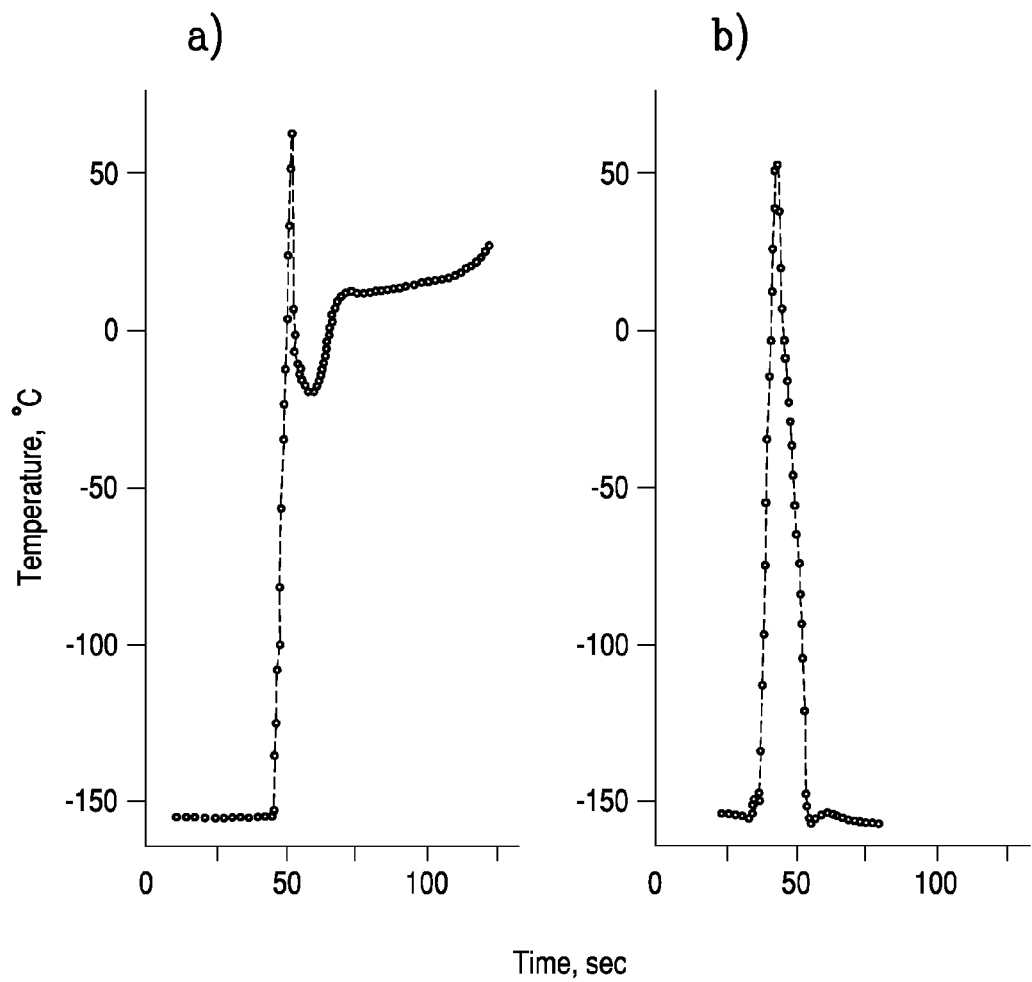
FIG. 7 displays experimental data illustrating certain properties of cryoprobes made in accordance with embodiments of the invention.
Figure 7:
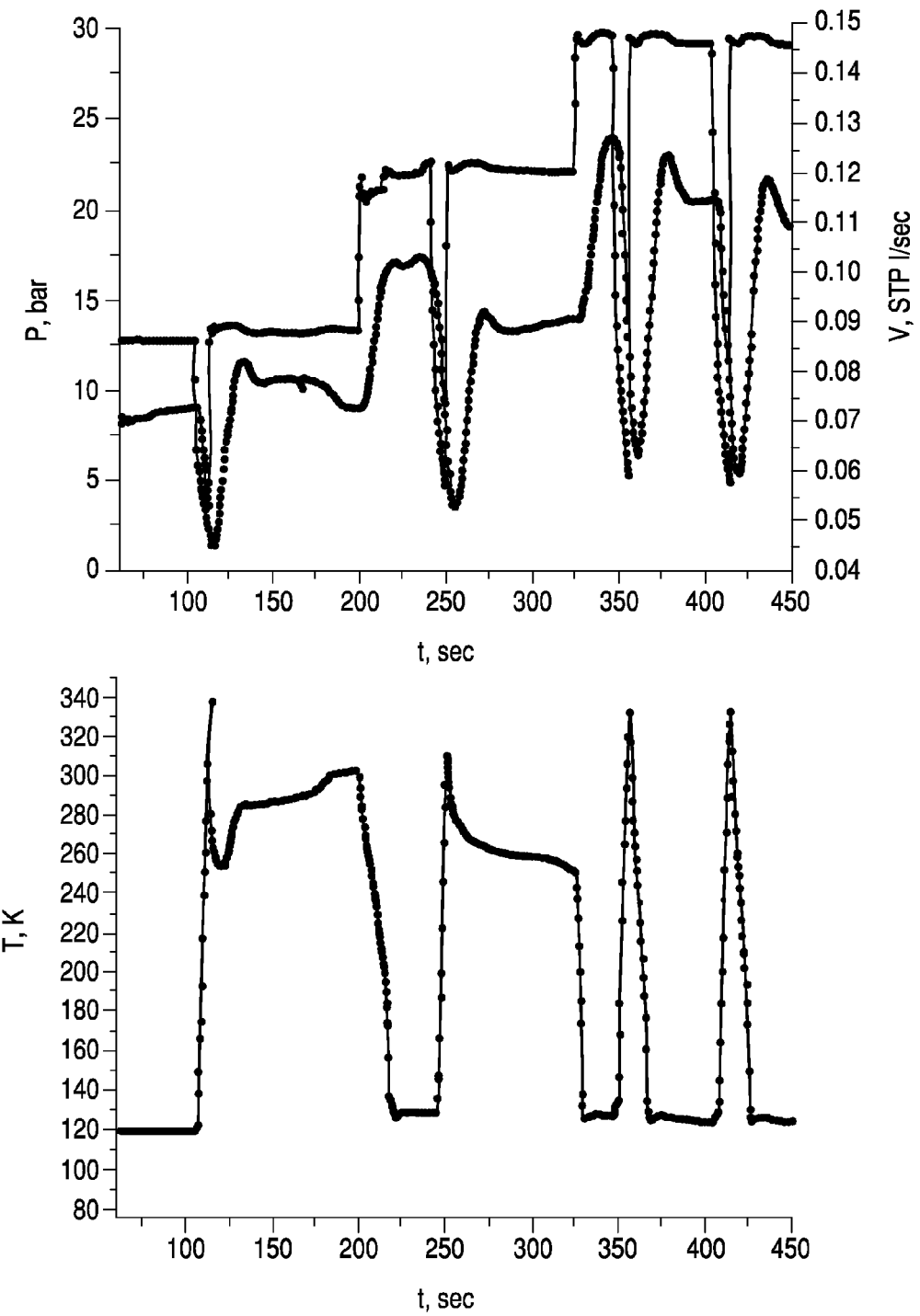

FIG. 7 provides data from experiments using the cryoprobe designs described above. The experimental data were taken with a 6.6-W heat load applied continuously to the tip of the probe, with the supply and return lines maintained within the vacuum-insulated shaft. Part (a) of the figure displays the tip temperature of the probe as a function of time during vapor lock recorded when the nitrogen pressure in the probe was 13 bar. At t=48 sec, the flow through the probe was momentarily stopped and then resumed after approximately 5 sec. As clearly seen, the heating of the probe's tip to approximately room temperature resulted in vapor lock, and the probe did not reachieve its deep freeze. The results for a similar procedure performed at 29 bar, i.e. near the critical pressure of 33.5 bar for nitrogen, are shown in part (b) of FIG. 7. A remarkably speedy recovery is evident from heating to about 50° C. to its freeze temperature of −153° C. In both cases, the flow rate through the probe was maintained on the level of about 10-15 STP L/sec. This demonstrates the advantage of operating near the critical point pressure to obtain reliable and rapid cooling power in the probe for all applications using rapid delivery of any liquid cryogens via a small tube, canula, needle, etc. We note that at the near-critical pressure of 29 bar, the time required to cool the probe tip under this heat load was exceptionally short (typically a few seconds), meeting the particular need for rapid freeze operations in cryosurgery. In part (c) of FIG. 7, the top plots display the pressure and the flow rate of the $LN_2$ in the probe, and the bottom plot displays the tip temperature of the probe. When the flow was cycled on and off momentarily at 13 bar (at time t=115 s), the probe vapor locked and did not reachieve its deep freeze temperature until the pressure was increased further to 22 bar at t=200 s. Even at this pressure, a momentary on and off cycle at t=250 s resulted in sluggishly slow cooling and an unacceptable base temperature of the probe until the pressure was increased to near 29 bar at t=325 s. At this pressure, very near the $LN_2$ critical pressure of 33.5 bar, the probe cycled rapidly between room temperature and 120 K (−150° C.) as the pressure was cycled. This further confirms the need for less than 2 mm to function at near-critical pressure for the initiation of a freeze, completely avoiding vapor lock.

Figure 8:
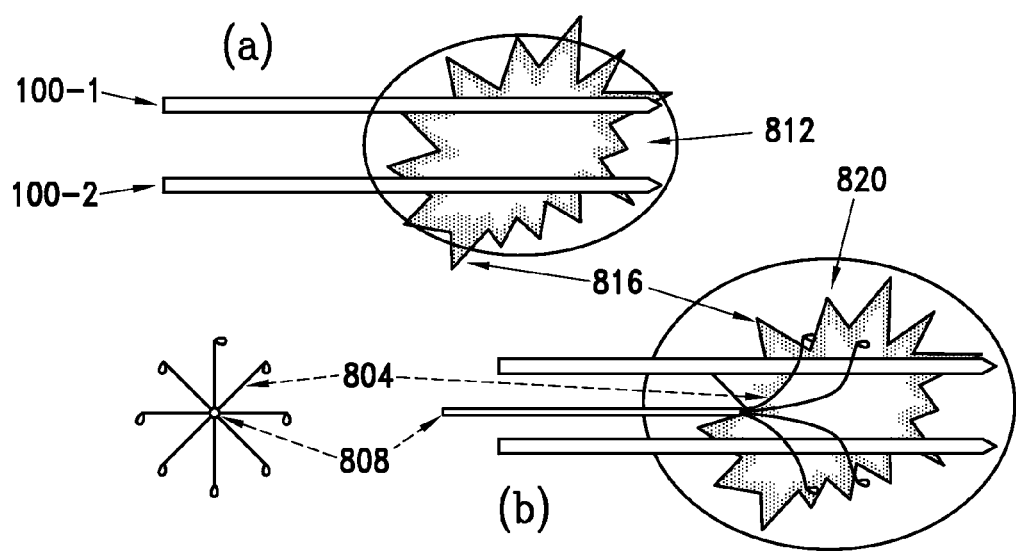
FIG. 8 provides an illustration of the use of cryoprobes within an irregular tumor.

In some embodiments, an injection-probe system, either within a separate probe or integrated into the vacuum jacketed space of the cryoprobe, may be used to improve ice distribution, an illustration of which is provided in FIG. 8. Part (a) of FIG. 8 shows two cryoprobes 100 within an irregular tumor 816 with ice 812 that fails to cover several margins of the tumor 816. Part (b) shows a separate injection probe system, with the left portion of the drawing showing a top view of the system and the right portion of the drawing showing a side view that illustrates the effect on the ice distribution 820. The separate injection probe system comprises a central probe 808 and a plurality of injection tines distributed radially and/or axially about the central probe 808. The use of the separate injection probe system easily allows the ice to propagate further, covering the entire tumor.

A variety of different fluid combinations may be delivered by the injection probe system. For example, macroaggregated albubin may be provided to decrease subsequent fluid extravasation by creating an interstitial gel effect, followed by a ~7% solution of NaCl containing 1:100,000 epiphrine, causing a significant decrease in heat sink effects through vascular constriction, as well as more thorough cytotoxicity via greater osmotic shock. Other fluids containing, but not limited to, chemotherapeutic or radiotherapeutic agents may also be delivered in a similar fashion. Also, the injection tines delivering the fluid do not need to be contained within a separate injection probe system, but could be alternatively be configured within the shaft of the cryoprobe. The resulting increase in cryoprobe diameter may be functionally offset by having a single insertion device for both recovered injection and cryotherapy.

A number of features and alternative embodiments to the specific embodiments described above, in both gas and liquid-based embodiments, are noted below.

1. Gas-based Embodiments i. Flow Control

For the embodiments displayed in FIGS. 2 and 3, the flow of gas through each of the cryoprobes inserted into the freeze zone is controlled by computer automation, and actuated by a manifold of flow control metering valves that are interfaced electronically to the computer. The return gas from each cryoprobe feeds into a return manifold, which passes through a chemical sieve configured to trap impurities in the gas within this closed cycle system. Many different gasses may be used in the closed cycle system, including nitrogen, argon, carbon dioxide, and multi-component gasses that have been prepared for the intended freeze operations. The computer program is designed to match the intended freeze zone specified by the physician by continuously varying the flow of gas through each of the multiple cryoprobes (or their individual JT ports within the each probe when there are multiple JT ports within a probe).

ii. Computer-imaging Interface

The computer interacts with pre-defined imaging parameters of ice expended as noted on standard cross-sectional imaging (i.e., US CT, or MRI). This includes the definition of freeze margins as their visualized phase change (i.e., solid: liquid) at the edge of the ice ball corresponding to approximately 0° C., or the assumed cytotoxic margin (i.e. <−40° C.) measuring ~5 mm behind the leading edge of the ice. Temperature mapping could take the form of currently defined MRI protocols, sound speed changes in ultrasound, or other image-related temperature functions. From a preoperative tumor mapping of the predicted ice extent (as seen in the FIG. 4), each probe can be driven to its appropriate maximum value to attain thorough, yet "sculpted" ice coverage of the tumor. The imaging documentation of the advancing freeze zone is thus compared with the original preoperative "planning model" in order to adjust the gas flow through each cryoprobe to achieve the desired freeze zone specified by the physician. Manual over ride capability may be provided to the physician in case the physician wants to manually control the gas flow through each JT port, and hence the freeze advance manually.

iii. Graphic User Interface (GUI)

A GUI is provided by the computer so that the physician may specify the intended freeze zone over a three dimensional rendering of the tissue, as determined from the imaging modality. The computer then assists with the distribution of the radiologically guided cryoprobe of whom placement, either manually or with robotic assist, and then notes the position of the freeze zone of each probe within the tissue, as shown in FIG. 4. This position information is provided to the thermophysical model of the tissue within the computer so that the computer may vary the flow rates through each probe to achieve the desired freeze region as specified by the physician. As previously noted in U.S. Ser. No. 10/757,768 entitled "CRYOTHERAPY PROBE," by Peter Littrup et al., which has been incorporated by reference, position sensors within each cryoprobe may better modify the final freeze parameters of each probe (intensity and duration) according to any position differences that may have occurred during placement, relative to their optimum position during treatment planning.

iv. Closed-cycle Compressor/filter System

The closed cycle compressor system comprises a multi-stage compressor with inner coolers (heat exchangers) between each stage of compression. A chemical filter sieve is located at the intake of the compressor and optimized to remove impurities from the closed-cycle flow system. Relevant temperatures, pressures, and flow rates within the compressor are monitored by the computer, and any evidence of compressor degradation may be reported back by the computer without operator intervention. Typically the compressor will require routine service once a year. The specific gas, and hence the optimal filter material, is determined by the specific medical applications, and may be changed if necessary through on-site service.

v. Compressor Requirements and Gas Mixture Optimization

Many facets of the previously described cryoprobe results in improved thermodynamic efficiency of the entire system, allowing a smaller compressor system due to the lower flow rate requirements from each probe. These include, but are not limited to: thermally insulated shaft of the cryoprobe; standard hydrodynamic codes and heat flow routines, to simultaneously optimize the heat exchanger (i.e., cooling power of about 15 to 30 W per probe at the base temperature of the probe) with the minimum flow impedance. This may be accommodated in some embodiments by supporting the cryoprobes with tubing of at least 0.5 cm inner diameter on the high pressure line, and at least 2.5 cm inner diameter on the return line, to assure laminar flow conditions to/from the compressor. These larger diameter tubes taper to the small dimensions of the cryoprobe at the cryoprobe's neck, assuring that the compressor doesn't have to work needlessly to support turbulent flow in the long lengths of tubing to/from the probe. For example, a 2.0 mm diameter cryoprobe with a 20 mm long active freeze zone (adequate to make about a 40 mm iceball) could use an argon flow rate of about 1 cfm. Once the multi-component gas mixture is made this can be even lower. One advantage of the gas mixtures are that they are much easier to compress. These gas mixtures have a much higher specific heat per unit volume and are far from an 'ideal gas' even at room temperature, which makes them more suitable for compression efficiency (i.e., the heat of compression is lower). With gas mixtures the possibility of clogging the JT port becomes much more of a problem, but our inserted wire safeguards against port fouling.

2. Liquid-Based Systems

Embodiments of a self-contained liquid-based cryotherapy system have been described in connection with FIGS. 6A-F. While the discussion has focused on $LN_2$, more generally any liquid cryogen could be used.

i. Flow Control

For the embodiments displayed in FIGS. 6A-6E, the flow of $LN_2$ through each of the cryoprobes inserted into the freeze zone is controlled by computer automation, and actuated by a manifold of flow control metering valves that are interfaced electronically to the computer. The $LN_2$ flow cryoprobe may be operated substantially continuously near its critical pressure of 33.5 bar, but the flow rate may be controlled by the computer adjustable flow impedance in the exhaust (or 'return') line from the cryoprobe. This adjustable flow impedance must be the largest flow impedance in the system to assure that the $LN_2$ within the probe is maintained very close to its critical pressure.

On initial cool-down, the flow impedance is set by the controlling computer at a low value, and the corresponding near critical $LN_2$ flow rate is very high. This assures the most rapid possible cool down of the probe, and hence the fastest possible freeze of the surrounding tissue. The probe reaches its base temperature near 77 K (−196 C) within a few seconds, and then the control computer increases the flow impedance to the maximum possible value while still maintaining the probe temperature at 77 K. This assures that the minimum flow rate of near critical $LN_2$ is used in each probe, providing for longer freeze times between dewar refills with $LN_2$. This flow rate of $LN_2$ is generally decreased with time by the controlling computer using this autonomous control scheme, since the maximum cooling power at the probe tip will decrease with time as the growing iceball partially insulates the cryoprobe from the tissue that is freezing at the periphery of the iceball. The controlling computer may continuously monitor the probe temperature during the freeze cycle, and if a sudden change in heat load to the probe occurs, then the resulting rise in the probe temperature may be counteracted by a reduction in the exhaust line flow impedance, thus increasing the flow rate in an adaptive way to assure the continued optimal performance of the cryoprobe on the minimum possible flow rate of the near critical $LN_2$. Similar automated control may be used during other cycles, such as the 'stick' cycle, where the probe is maintained at about −10° C. in order to assure that the probe placement remains firm, and in the thaw cycle, where the $LN_2$ flow is stopped entirely by closing the flow impedance on the exhaust line completely (infinite impedance) and then increasing the current through the wrapped wire heater for a time interval that has been pre-determined by the controlling computer to result in the thaw of the tissue to a target thaw depth away from the probe.

ii. Computer-imaging Interface

The computer interacts with pre-defined imaging parameters of ice expended as noted on standard cross-sectional imaging (i.e., US, CT, or MRI). This includes the definition of freeze margins as their visualized phase change (i.e., solid: liquid) at the edge of the ice ball corresponding to approximately 0° C., or the assumed cytotoxic margin (i.e. <−40° C.) measuring ~5 mm behind the leading edge of the ice. Temperature mapping could take the form of thermometer readings, currently defined MRI protocols, future sound speed changes in ultrasound, or other image-related temperature functions. From a preoperative tumor mapping of the predicted ice extent (as seen in FIG. 4), each probe can be driven to its appropriate maximum value to attain thorough, yet "sculpted" ice coverage of the tumor. The imaging documentation of the advancing freeze zone is thus compared with the original preoperative "planning model" in order to adjust the $LN_2$ flow through each cryoprobe to achieve the desired freeze zone specified by the physician. Manual over ride capability may be provided to the physician in case the physician wants to manually control the $LN_2$ flow through each probe, and hence manually advance the freeze.

iii. Graphic User Interface (GUI)

A GUI is provided by the computer so that the physician may specify the intended freeze zone over a three dimensional rendering of the tissue, as determined from the imaging modality. The computer then assists with the distribution of the radiologically guided cryoprobe of whom placement, either manually or with robotic assist, and then notes the position of the freeze zone of each probe within the tissue, as shown in FIG. 4. This position information is provided to the thermophysical model of the tissue within the computer so that the computer may vary the flow rates through each probe to achieve the desired freeze region as specified by the physician. As previously noted in Ser. No. 10/757,768 entitled "CRYOTHERAPY PROBE," by Peter Littrup et al., which has been incorporated by reference, position sensors within each cryoprobe may better modify the final freeze parameters of each probe (intensity and duration) according to any position differences that may have occurred during placement, relative to their optimum position during treatment planning.

iv. Closed- or Open-cycle Compressor/filter System

Unlike the gas-based system, efficient utilization of $LN_2$ via our near-critical approach allows a self-contained unit for both large applications, as well as a compact, convenient system for nerve applications, or other non-medical uses requiring only short freeze bursts on the order of seconds, rather than several minutes. Our current estimates of $LN_2$ utilization is 2 liter of $LN_2$ should be sufficient to power one probe at ~25 Watts continuous cooling power for at least 60 minutes. This appears scalable, such that a single charge of 5-10 gallons of $LN_2$ would be adequate for 3 typical prostate case without refilling (i.e., assuming 6 probes, ~15-2.0 mm diameter, and 2 cycles of 20 minute freezes per case).

v. Compressor Requirements and Optimization

Many facets of the previously described cryoprobe results in improved thermodynamic efficiency of the entire system, allowing a smaller compressor system due to the lower flow rate requirements from each probe. These include similar arrangements for all liquid cryogens, and are not limited to the below described $LN_2$ system.

The $LN_2$ compressor system operating at cryogenic temperatures, may be used to boost the pressure of $LN_2$ at 77K from one atmosphere to the same temperature at a pressure at or near its critical point pressure of 33.5 bars. Liquid nitrogen is nearly non-compressible over this pressure range, meaning not much volume change is required to compress ambient $LN_2$ to its critical pressure. The heat of compression of $LN_2$ is relatively small at 181 J per liquid liter compressed. The post-compression heat exchanger may evaporate about 0.8 liters of ambient $LN_2$ per hour to support a near critical flow of $LN_2$ through the cryoprobe at a rate of about 0.2 STP liters per second, which is typical for this cryosurgical application. Hence the compressor described in connection with FIG. 6B is intended to support a flow of 0.2 STP liters per second per cryoprobe at near critical pressure. This system may support up to eight such probes operating simultaneously, so the full capacity of the $LN_2$ compressor described below is 1.6 STP liters per second, with adequate post-compression heat exchange with the $LN_2$ bath to remove the associated heat of compression, resulting in a near critical, supercooled stream of $LN_2$ at a pressure near the liquid/vapor critical pressure of 33.5 bar, but supercooled at the inlet to 77 K. This design is scalable to other larger and smaller flow applications, so the use of the innovations associated with this $LN_2$ compressor design for different rates of flow should be considered obvious to one skilled in the art.

The controlling computer that operates this system controls the rate of the stepper motor advance, and performs the reversal of the stepper motor direction once the compression of the compression bellow is near its maximum level. This controlling computer monitors the force exerted by the stepper motor, using either the direct stepper motor calibration or a shaft load cell readout, to assure that this applied force divided by the end area of the bellows matches the designed operating pressure of the system (which is near 33.5 atmospheres). The controlling computer adjusts the stepper motor controller appropriately to exert this constant force continuously in either direction while monitoring the position of the common endplate displacement in order to determine when a direction reversal is required. A similar design procedure may be applied to all other liquid-vapor cooling systems to create supercooled liquid at or near its critical pressure within the container/heat exchanger following compression.

Supercooled, near critical liquid is then supplied to the cryoprobe through a vacuum jacketed line running from the container/heat exchanger to the cryoprobe's input line. The flow rate of the near critical $LN_2$ through the probe is limited by a flow controller on the outlet flow from the probe. This flow controller may operate in steady state by providing the largest flow impedance within this flow circuit to guarantee that the $LN_2$ within the probe is approximately at the same near critical pressure as the $LN_2$ in the container/heat exchanger, with the pressure drop through the vacuum Jacketed supply line and the probe being a small fraction of the absolute pressure near the critical pressure.

vi. Enhancement of Freeze Probe Tissue Kill Rate with Electrical Ablation

The vacuum insulated shaft of the cryoprobes may be made of an electrical insulating material, such as a ceramic or a composite material. This will permit the electrically conducting probe tip to be used as an electrode in an electrical ablation application. Once multiple probes have been placed within the tumor tissue, an electrical current may be forced to flow from one probe tip to another. This may be driven to cause enough interposed tissue heating to generate some coagulation, thus reducing the blood flow through the region primarily between the probe tips. However, this may elicit pain despite making the tissue much easier to freeze. The heating function may then be better utilized after an initial quick freeze and then cycled on and off. Once the freeze has resulted in an iceball between the probe tips, another electrical current may be passed between the probe tips to destroy tissue at the periphery of the freeze zone, and to further attenuate blood flow at the periphery of the tumor around the ice margin. In this application, once an iceball exists between the probe tips, then the frozen tissue is a much worse electrical conductor than the tissue surrounding the iceball. Hence, the electrical current will flow from one probe tip to the other, primarily in the periphery of the tumor, helping destroy tissue and blood flow in this peripheral region. An optimal electrical ablation/cryogenic ablation sequence may thus include alternating freeze periods and electrical ablation periods. This optimal sequence will be determined by the physician during the tumor ablation procedure, based primarily on the efficacy of generating the largest feasible ablation zone as determined by near real time imaging of the tissue being ablated.

The methods of the present invention may be embodied in a computer-readable storage medium having a computer-readable program embodied therein for directing operation of a cryotherapy system such as described above. The computer-readable program includes instructions for operating the cryotherapy system in accordance with the embodiments described above.

Thus, having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A computer-readable storage medium having a computer-readable program embodied therein for directing operation of a cryotherapy system including a plurality of cryoprobes, each such cryoprobe having a shaft with a closed distal end adapted for insertion into a body and conduits for flowing a cryogenic fluid through the shaft to reduce a temperature of the distal end, a source of the cryogenic fluid, a plurality of flow-control metering valves in fluid communication with the conduits of the plurality of cryoprobes and with the source of the cryogenic fluid, a compressor in fluid communication with the conduits of the plurality of cryoprobes to define a self-contained fluid system, and a computer processor, wherein the computer-readable program includes:
   instructions for controlling the plurality of flow-control metering valves and the compressor to provide desired flows of the cryogenic fluid through the conduits of the self-contained fluid system and
   instructions to control the compressor and the plurality of flow-control metering valves to provide an initial flow of the cryogenic fluid through the conduits of the cryoprobes under physical conditions near a critical point of a liquid-vapor system for the cryogenic fluid, wherein the critical point defines a point in a phase diagram of the liquid-vapor system where molar volumes are substantially equivalent for liquid and gas,
   whereby vapor lock associated with freezing of the cryoprobes is avoided.

2. The computer-readable storage medium recited in claim 1 wherein the self-contained fluid system is an open-loop system.

3. The computer-readable storage medium recited in claim 1 wherein the self-contained fluid system is a closed-loop system.

4. The computer-readable medium recited in claim 1 wherein:
   the cryogenic fluid is a gas;
   each such cryoprobe further has a heat exchanger disposed within the shaft in thermal communication with the conduits of such cryoprobe and has a Joule-Thomson port disposed in the distal end of the shaft in thermal communication With the heat exchanger; and
   the computer-readable program further has instructions for controlling operation of each of the Joule-Thomson ports.

5. The computer-readable storage medium recited in claim 1 wherein:
   the cryogenic fluid is a liquid; and
   the computer-readable program further has instructions for controlling the compressor and plurality of flow-control metering valves to provide an initial flow of the liquid through the conduits of the cryoprobes under physical conditions near a critical point of a liquid-vapor system for the liquid, whereby vapor lock associated with freezing of the cryoprobes is avoided.

6. The computer-readable storage medium recited in claim 5 wherein the computer-readable program further has instructions for controlling the compressor and plurality of flow-control metering valves to reduce a pressure of the liquid in the cryoprobes, whereby colder liquid temperatures may be maintained without vapor lock after the initial flow is established.

7. The computer-readable storage medium recited in claim 1 wherein the computer-readable program further has instructions for determining the desired flows from predefined imaging parameters.

8. The computer-readable storage medium recited in claim 1 wherein:
   each of the plurality of cryoprobes further has a plurality of multifunction electrical wires; and
   the computer-readable program further has instructions for monitoring the operation of the multifunction electrical wires.

* * * * *